United States Patent
Ding et al.

(10) Patent No.: US 7,365,082 B2
(45) Date of Patent: Apr. 29, 2008

(54) N-(SUBSTITUTED ARYLMETHYL)-4-(DISUBSTITUTED METHYL)PIPERIDINES AND PIPERAZINES

(75) Inventors: Ping Ding, Lawrenceville, NJ (US); Robert N. Henrie, II, Pennington, NJ (US); Daniel H. Cohen, Princeton, NJ (US); John W. Lyga, Basking Ridge, NJ (US); David S. Rosen, Kendall Park, NJ (US); George Theodoridis, Princeton, NJ (US); Qun Zhang, Princeton, NJ (US); Walter H. Yeager, Yardley, PA (US); Stephen F. Donovan, Revere, PA (US); Steven Shunxiang Zhang, Plainsboro, NJ (US); Inna Shulman, Langhorne, PA (US); Seong Jae Yu, Pennington, NJ (US); Guozhi Wang, Freshmeadow, NY (US); Y. Larry Zhang, Kendall Park, NJ (US); Ariamala Gopalsamy, Mahwah, NJ (US); Dennis L. Warkentin, East Windsor, NJ (US); Paul E. Rensner, Yardley, PA (US); Ian R. Silverman, Moorestown, NJ (US); Thomas G. Cullen, Milltown, NJ (US)

(73) Assignee: Bayer CropScience AG, Monheim (DE)

(*) Notice: Subject to any disclaimer, the term of this patent is extended or adjusted under 35 U.S.C. 154(b) by 0 days.

(21) Appl. No.: 10/538,997

(22) PCT Filed: Dec. 8, 2003

(86) PCT No.: PCT/US03/39046

§ 371 (c)(1),
(2), (4) Date: Feb. 8, 2006

(87) PCT Pub. No.: WO2004/060865

PCT Pub. Date: Jul. 22, 2004

(65) Prior Publication Data

US 2006/0166962 A1 Jul. 27, 2006

Related U.S. Application Data

(60) Provisional application No. 60/495,059, filed on Aug. 14, 2003, provisional application No. 60/434,718, filed on Dec. 18, 2002.

(51) Int. Cl.
*A61K 31/44* (2006.01)
*A61K 31/445* (2006.01)
*A61K 31/4422* (2006.01)
*C07D 211/06* (2006.01)
*C07D 211/08* (2006.01)
*C07D 211/70* (2006.01)
*C07D 211/82* (2006.01)

(52) U.S. Cl. ............... 514/317; 514/331; 546/229; 546/237

(58) Field of Classification Search ............... 514/326, 514/315; 546/184, 210
See application file for complete search history.

(56) References Cited

U.S. PATENT DOCUMENTS

| 5,939,438 A | 8/1999 | Yeager et al. |
| 6,017,831 A | 1/2000 | Beardsley et al. |

FOREIGN PATENT DOCUMENTS

| EP | 0 296 721 | 12/1988 |
| EP | 0 979 819 | 2/2000 |

OTHER PUBLICATIONS

Kuroyan et al. Armyanskii Khimicheskii Zhurnal (1983), 36(9), 614-17.*

* cited by examiner

*Primary Examiner*—Rebecca Anderson
*Assistant Examiner*—Yong Chu
(74) *Attorney, Agent, or Firm*—Sterne, Kessler, Goldstein & Fox P.L.L.C.

(57) ABSTRACT

It has now been found that certain novel N-(substituted aryl)-4-(disubstituted methyl)piperidine and pyridine derivatives have provided unexpected insecticidal activity. These compounds are represented by formula (I): wherein m, n, q, r, and s are independently selected from 0 or 1; and p is 0, 1, 2, or 3; A is CH or N; and B, D, E, R, $R^1$, $R^2$, $R^3$, $R^4$, $R^5$, $R^6$, $R^7$ and $R^8$ are fully described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

9 Claims, No Drawings

N-(SUBSTITUTED ARYLMETHYL)-4-(DISUBSTITUTED METHYL)PIPERIDINES AND PIPERAZINES

This application is a 35 U.S.C. §371 U.S. National Phase filing of International Application No. PCT/US2003/039046, filed Dec. 8, 2002, which claims the benefit of U.S. Provisional Patent Application No. 60/434,718, filed Dec. 18, 2002 and U.S. Provisional Patent Application No. 60/495,059, filed Aug. 14, 2003.

FIELD OF THE INVENTION

The present invention generally relates to insecticidal compounds and their use in controlling insects. In particular, it pertains to insecticidal N-(substituted aryl)-4-(disubstituted methyl)piperidines and piperazine derivatives, N-oxides, and agriculturally acceptable salts thereof, compositions of these insecticides, and methods for their use in controlling insects.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Thus, there is a continuing demand for new insecticides that are safer, more effective, and less costly. Insecticides are useful for controlling insects which may otherwise cause significant damage to crops such as wheat, corn, soybeans, potatoes, and cotton to name a few. For crop protection, insecticides are desired which can control the insects without damaging the crops, and which have no deleterious effects to mammals and other living organisms.

A number of patents disclose a variety of insecticidally active substituted piperidine and piperazine derivatives. For example, as set forth in U.S. Pat. No. 5,569,664, compounds of the following structure are reported to be insecticidally active:

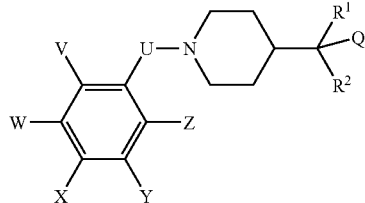

where U is selected from —(CH$_2$)$_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; W is selected from hydrogen, halogen, alkyl, haloalkyl, alkoxy, nitro, amino, phenoxy, and phenylalkoxy; X is selected from hydrogen, hydroxy, halogen, alkyl, alkoxyalkyl, alkoxy, cycloalkylalkoxy, haloalkoxy, alkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkoxycarbonylamino, alkylcarbonyl, alkoxycarbonyl, alkylaminocarbonyl, aminocarbonyloxy, phenyl, phenylalkoxy, phenoxy, and phenoxyalkyl; Y and Z are independently selected from hydrogen and alkoxy; R$^1$ and R$^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

As set forth in U.S. Pat. No. 5,639,763 compounds of the following structure are reported to be insecticidally active:

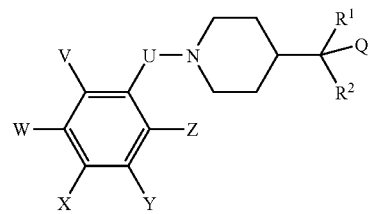

where U is selected from —(CH$_2$)$_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; Y and Z are independently selected from hydrogen and alkoxy; W and X taken together is —OCH$_2$CH$_2$O—, —CH$_2$C(CH$_3$)$_2$ O—, —OC(CH$_3$)$_2$O—, or —N=C(C$_2$H$_5$)O—; R$^1$ and R$^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

As set forth in U.S. Pat. No. 5,795,901 compounds of the following structure are reported to be insecticidally active:

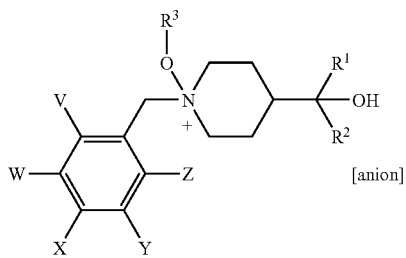

where V, W, Y, and Z are hydrogen; X is alkoxy, cycloalkoxy, alkoxycarbonyl, alkoxycarbonylamino, or a five- or six-membered heteroaryl or heteroaryloxy, each heteroaryl optionally substituted with halogen, cyano, alkyl, haloalkyl, alkoxy, haloalkoxy, alkoxyalkyl, or haloalkoxyalkyl; R$^1$ and R$^2$ are independently selected from haloalkyl, phenyl substituted with halogen, halothio, haloalkyl, or haloalkoxy; or a five- or six-membered heteroaryl substituted with halogen or alkyl; R$^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, arylcarbonyl, sulfonato, or sulfonatoalkyl, and may bear a negative charge resulting in an inner salt, and a separate anion is chloride, bromide, iodide, or a phenyl, or alkyl sulfate or sulfonate.

As set forth in U.S. Pat. No. 5,939,438 compounds of the following structure are reported to be insecticidally active:

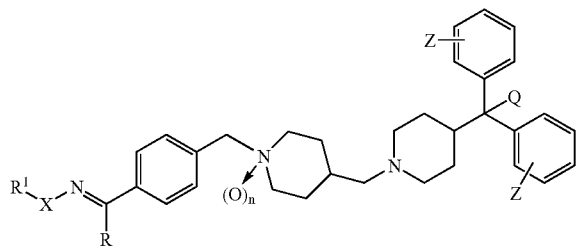

where R is hydrogen, halogen, alkyl, alkoxy, or dialkylamino; $R^1$ is hydrogen, alkyl, haloalkyl, alkoxyalkyl, alkylcarbonyl, or alkylaminocarbonyl; Q is fluoro or hydroxy; X is oxygen or $NR^2$; Z is halogen, haloalkyl, haloalkoxy, pentahalothio, haloalkylthio, haloalkylsulfinyl, haloalkylsulfonyl, or —$OCF_2O$— attached to two adjacent carbon atoms of the phenyl ring; n is 0 or 1; and, when X is $NR^2$, $R^2$ is hydrogen, alkyl, alkylcarbonyl, alkoxycarbonyl, or $R^1$ and $R^2$ taken together may be —$C_mH_{2m}$—, or —$C_2H_4OC_2H_4$—, where m is 3-9; and their agriculturally acceptable salts.

As set forth in U.S. Pat. No. 6,017,931 compounds of the following structure are reported to be insecticidally active:

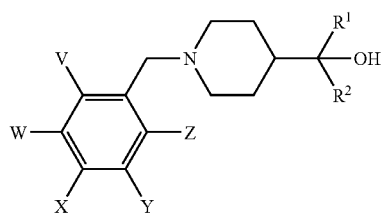

where V, W, and Z are hydrogen; X is selected from alkoxy, haloalkoxy, alkoxyalkyl, cycloalkylalkoxyl, halocycloalkylalkoxy, alkoxycarbonyl, haloalkoxycarbonyl, cycloalkylalkoxylcarbonyl, halocycloalkylalkoxylcarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen; Y is selected from hydrogen or halogen; $R^1$ and $R^2$ are independently selected from phenyl or pyridyl, each substituted with haloalkyl, haloalkoxy, or alkylthio, and the corresponding N-oxides and agriculturally acceptable salts.

As set forth in U.S. Pat. No. 6,030,987 compounds of the following structure are reported to be insecticidally active:

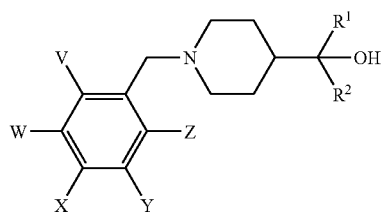

where V, W, Y and Z are hydrogen; X is a five- or six-membered heterocycle optionally substituted with halogen, alkyl, alkoxy, alkoxyalkyl, cyano, aminocarbonyl, haloalkyl, haloalkoxy, or haloalkoxyalkyl, and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from phenyl or pyridyl, each substituted with haloalkyl, or haloalkoxy; $R^3$ and $R^4$ are independently selected from hydrogen and methyl; n and p are independently 1, 2, or 3; and q is 1 or 2, and the corresponding N-oxides and agriculturally acceptable salts.

As set forth in U.S. Pat. No. 6,184,234 compounds of the following structure are reported to be insecticidally active:

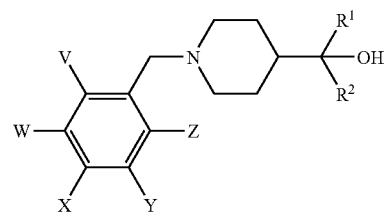

where V, W, Y and Z are hydrogen; X is a five- or six-membered heterocycle optionally substituted with bromine, chlorine, fluorine, alkyl, alkoxy, alkoxyalkyl, cyano, aminocarbonyl, haloalkyl, haloalkoxy, or haloalkoxyalkyl; and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from i) phenyl or pyridyl, each substituted with pentahalothio, haloalkylthio, haloalkylsulfinyl, or haloalkylsulfonyl; ii) phenyl substituted with —$OC(M)_2O$—, where M is bromine, chlorine, or fluorine to provide a dihalobenzodioxolyl fused ring; or iii) pyridyl substituted with —$OC(M)_2O$—, to provide a dihalodioxoleneopyridyl fused ring; $R^3$ and $R^4$ are independently selected from hydrogen and methyl; n and p are independently 1, 2, or 3; and q is 1 or 2, and the corresponding N-oxides and agriculturally acceptable salts.

As set forth in United States Statutory Invention Registration H1,838 compounds of the following structure are reported to be insecticidally active:

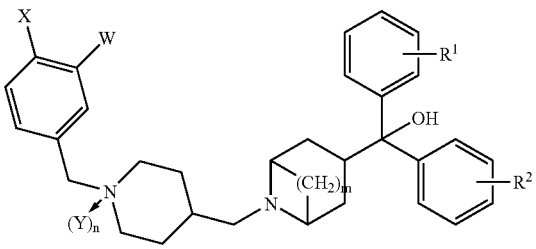

where m is 2 or 3; n is 0 or 1; X is hydrogen, alkoxy, cycloalkylalkoxy, haloalkoxyimino, or a five- or six-membered heteroaryl or heteroaryloxy in which one or more hetero atoms may be optionally substituted with alkyl; $R^1$ and $R^2$ are independently selected from hydrogen, haloalkyl, halothio, or haloalkoxy; and when n is 1, Y represents (a) an N-oxide of the ring nitrogen; or (b) an agriculturally acceptable anionic salt of the ring nitrogen; or (c) forms an $OR^3$ linkage in which $R^3$ is selected from hydrogen, alkyl, alkoxycarbonylalkyl, hydroxycarbonylethyl in association with an agriculturally acceptable anion resulting in an ionic salt, or R is an oxycarbonylalkyl group bearing a negative charge resulting in an inner salt.

As set forth in United States Statutory Invention Registration H1,996 photostable, agriculturally acceptable acid salts of an organic or inorganic acid of the following structure are reported to be insecticidally active:

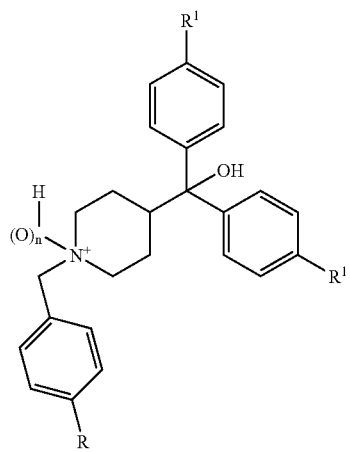

where R is alkoxycarbonyl, alkoxycarbonylamino, cycloalkylalkoxy, 2-alkyl-2H-tetrazol-5-yl, or 2-haloalkyl-2H-tetrazol-5-yl; $R^1$ is trihaloalkyl, or trihaloalkoxy; n is 0, or 1; and said salt is at least 2.5 times more photostable than its non-ionic parent and is derived from hydrochloric acid, hydrobromic acid, boric acid, phosphoric acid, maleic acid, fumaric acid, phthalic acid, D)-glucuronic acid; the sulfonic acid $R^2SO_3H$ where $R^2$ is alkyl, haloalkyl, hydroxyalkyl, D-10-camphoryl, or phenyl optionally substituted with alkyl or halogen; the carboxylic acid $R^3CO_2H$ where $R^3$ is hydrogen, alkyl, trihaloalkyl, carboxyl, phenyl optionally substituted with alkyl or halogen, or pyridyl; the boronic acid $R^4B(OH)_2$ where $R^4$ is alkyl or phenyl optionally substituted with alkyl or halogen; the phosphonic acid $R^5PO_3H_2$ where $R^5$ is alkyl, haloalkenyl, or phenyl optionally substituted with alkyl or halogen; the sulfuric acid $R^6OSO_3H$ where $R^6$ is hydrogen or alkyl; or the alkanoic acid $X$—$(CH_2)_qCO_2H$ where q is 0 to 11, X is halogen, trihaloalkyl, haloalkenyl, cyano, aminocarbonyl, or $CO_2R^7$ where $R^7$ is hydrogen or alkyl.

As set forth in United States Statutory Invention Registration H2,007 compounds of the following structures are reported to be insecticidally active:

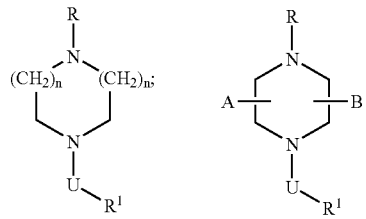

where A and B are independently selected from lower alkyl; U is selected from lower alkylidene, lower alkenylidene, and CH-Z, where Z is selected from hydrogen, lower alkyl, lower cycloalkyl, or phenyl; R is —$CHR^3R^4$ where $R^3$ and $R^4$ are are independently selected from phenyl, optionally substituted with halogen, lower alkyl, lower haloalkyl, lower alkoxy, lower haloalkoxy, lower alkenyl, or phenyl; $R^1$ is phenyl, naphthyl, tetrazolylphenyl, phenylcyclopropyl, phenoxyphenyl, benzyloxyphenyl, pyridylphenyl, pyridyloxyphenyl, or thiadiazolyloxyphenyl, each optionally substituted with halogen, cyano, hydroxy, lower alkyl, lower haloalkyl, lower alkoxy, amino, lower dialkylamino, nitro, lower haloalkylsulfonyloxy, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R^1$ groups; m is 2 or 3; and n is 1, 2, or 3.

As set forth in unexamined Japanese Patent Application 2002-220372 compounds of the following structures are reported to be insecticidally active:

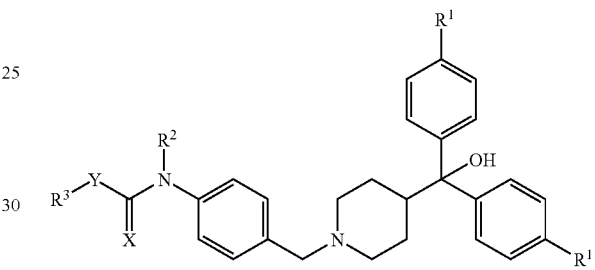

where $R^1$ and $R^2$ are independently selected from hydrogen, halogen, lower alkyl, lower haloalkyl, lower alkoxy, lower haloalkoxy, or lower alkylsulfonyloxy; $R^2$ is selected from hydrogen, lower alkyl, lower alkenyl, lower alkoxyalkyl, or lower alkylcarbonyl; X and Y are independently oxygen or sulfur; $R^3$ is selected from lower alkenyl, or lower alkynyl, which are optionally substituted with hydroxy, halogen, lower alkoxy, lower haloalkoxy, lower alkylthio, lower alkylsulfinyl, lower alkylsulfonyl, lower cycloalkyl, lower alkoxyalkoxy, amino, lower alkylamino, lower dialkylamino, lower alkoxycarbonyl, nitro, cyano, trimethylsilyl, phenyl, or lower cycloalkenyl; and the corresponding N-oxides and salts.

As set forth in PCT Publication WO 02/068392A1 compounds of the following structures are reported to be insecticidally active:

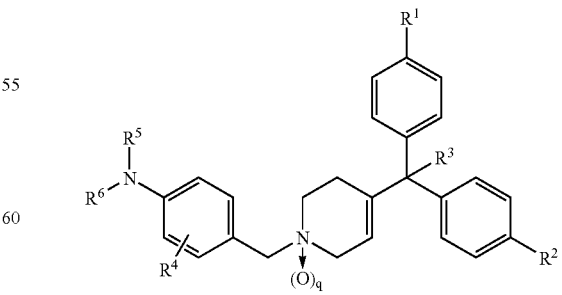

where $R^1$ and $R^2$ are independently selected from halogen, $C_1$-$C_6$alkyl, halo$C_1$-$C_6$alkyl, $C_1$-$C_6$alkoxy, halo$C_1$-$C_6$alkoxy, —$S(=O)_p$—$R^9$, or $SF_5$; $R^3$ is hydrogen, hydroxy, $C_1$-$C_6$alkoxy, or —OC(=O)—$C_1$-$C_6$alkyl; $R^4$ is hydrogen, halogen, $C_1$-$C_6$alkyl, halo$C_1$-$C_6$alkyl, $C_1$-$C_6$alkoxy, halo$C_1$-$C_6$alkoxy, or S(=O)$_p$—$R^9$, or —SCN; $R^5$ and $R^6$ are independently selected from $C_1$-$C_{12}$alkyl, halo$C_1$-$C_{12}$alkyl, $C_2$-$C_{12}$alkenyl, halo$C_2$-$C_{12}$alkenyl, $C_2$-$C_{12}$alkynyl, halo$C_2$-$C_{12}$alkynyl, $C_3$-$C_8$cycloalkyl, —C(=O)—OR$^7$, —C(=S)—OR$^8$, —C(=Y)-ZR$^8$, —S(=O)$_p$—R$^9$, aryl, aryl$C_1$-$C_6$alkyl, heterocycle, heterocycle to five times independently of one another by halogen, hydroxy, cyano, nitro, $C_1$-$C_6$alkyl, halo$C_1$-$C_6$alkyl, $C_1$-$C_6$alkoxy, halo$C_1$-$C_6$alkoxy; or in common together with the nitrogen atom to which they are attached to form a heterocyclic ring which is substituted or unsubstituted; Y is oxygen or sulfur; X is a bond, —NR$^{10}$—, or sulfur; $R^7$ is $C_1$-$C_6$alkoxy-$C_1$-$C_6$alkyl, $C_1$-$C_6$alkylthio-$C_1$-$C_6$alkyl, $C_1$-$C_6$alkylamino-$C_1$-$C_6$alkyl, $C_3$-$C_6$alkynyl, $C_1$-$C_6$alkyl-S(=O)$_p$—$C_1$-$C_6$alkyl, $C_3$-$C_8$cycloalkyl, aryl, aryl-$C_1$-$C_6$alkyl, heterocyclyl, or heterocyclyl-$C_1$-$C_6$alkyl each substituted in the ring from one to five times independently of one another by halogen, cyano, nitro, $C_1$-$C_6$alkyl, halo$C_1$-$C_6$alkyl, $C_1$-$C_6$alkoxy, or halo$C_1$-$C_6$alkoxy; $R^8$ is $C_1$-$C_6$alkyl, halo$C_1$-$C_6$alkyl, $C_1$-$C_6$alkoxy-$C_1$-$C_6$alkyl, $C_1$-$C_6$alkylthio-$C_1$-$C_6$alkyl, $C_2$-$C_6$alkenyl, $C_3$-$C_6$alkynyl, $C_1$-$C_6$alkyl-S(=O)$_p$-$C_1$-$C_6$alkyl, $C_3$-$C_8$cycloalkyl, aryl, aryl-$C_1$-$C_6$alkyl, heterocyclyl, or heterocyclyl-$C_1$-$C_6$alkyl, or is $C_3$-$C_8$cycloalkyl, aryl, aryl-$C_1$-$C_6$alkyl, heterocyclyl, or heterocyclyl-$C_1$-$C_6$alkyl each substituted in the ring from one to five times independently of one another by halogen, cyano, nitro, $C_1$-$C_6$alkyl, halo$C_1$-$C_6$alkyl, $C_1$-$C_6$alkoxy, or halo$C_1$-$C_6$alkoxy; $R^9$ is $C_1$-$C_6$alkyl, $C_3$-$C_8$cycloalkyl, halo$C_1$-$C_6$alkyl, or benzyl; $R^{10}$ is hydrogen, $C_1$-$C_6$alkyl, $C_3$-$C_8$cycloalkyl, halo$C_1$-$C_6$alkyl, or benzyl; p is 0, 1, or 2; q is 0 or 1; and, where apporopriate, E/Z isomers, E/Z isomer mixtures and/or toutomers, each in free form or in salt form.

As set forth in PCT Publication WO 200020409A1 compounds of the following structures are reported to be insecticidally active:

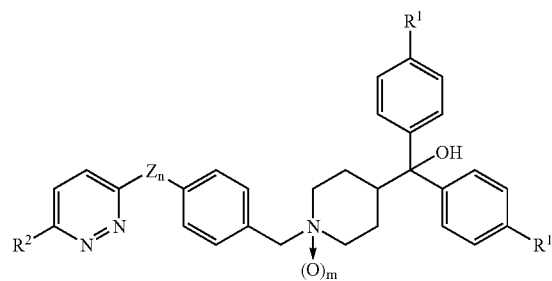

where $R^1$ is halo, $C_1$-$C_4$alkyl, $C_1$-$C_4$alkoxy, $C_1$-$C_4$haloalkyl, $C_1$-$C_4$haloalkoxy; $R^2$ is hydrogen, hydroxyl, halo, $C_1$-$C_4$alkyl, $C_1$-$C_4$alkoxy, $C_1$-$C_4$alkoxycarbonyl, $C_1$-$C_4$alkylthio, $C_1$-$C_4$alkylsulfonyl, optionally substituted phenyl or carbamoyl; Z is O or S(O)$_p$, p is 0 or 2; and m and n are 0 or 1.

As set forth in PCT Publication WO 03/022808A1 compounds of the following structures are reported to be pesticidally active:

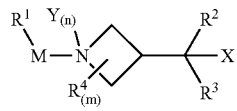

where $R^1$ represents aryl or heteroaryl that is optionally identically or differently substituted once or several times; $R^2$ and $R^3$ are identical of different and represent aryl or heteroaryl that is optionally identically or differently substituted once or several times, whereby both groups can also be bridged by a common substituent; M is optionally substituted (CH$_2$)$_l$, where l is 1, 2, or 3, CO, or —HN—C(O); X represents H, OH, halogen, OR4 or CN; Y represents (O), H, OH, OR$^4$, R$^4$; (in the last four groups, in which nitrogen has a positive charge, in combination with a corresponding anion); $R^4$ is identical or different and represents ($C_1$-$C_4$) alkyl, ($C_1$-$C_4$)alkanoyl, ($C_1$-$C_4$)haloalkyl; m is 0, 1, 2, 3; and n 0 or 1.

As set forth in published Japanese Patent Application JP 62,145,018, the following compound is disclosed as being an antiallergy pharmaceutical agent:

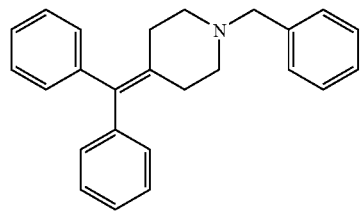

There is no disclosure or suggestion in any of the citations set forth above of the piperidine or pyridine derivatives of the present invention.

SUMMARY OF THE INVENTION

In accordance with the present invention, it has now been found that certain N-(substituted arylmethyl)-4-(disubstituted methyl)piperidine and piperazine derivatives, (hereinafter termed "compounds of formula I"), N-oxides, and agriculturally acceptable salts thereof are surprisingly active when used in the insecticidal compositions and methods of this invention. The compounds of formula I are represented by the following general formula I:

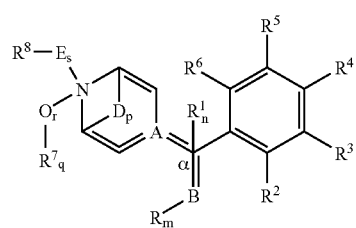

I wherein;

m, n, q, r, and s are independently selected from 0 or 1; and p is 0, 1, 2, or 3;

A is CH or N, forming a six-membered azine ring selected from piperidine or piperazine;

$R^2$, $R^3$, $R^4$, $R^5$, and $R^6$ are independently selected from hydrogen, halogen, alkyl, haloalkyl, hydroxyl, alkoxy, haloalkoxy, pentahalothio, alkylthio, cyano, nitro, alkylcarbonyl, alkoxycarbonyl, aryl, or aryloxy, and, wherein either of $R^2$ and $R^3$, or $R^3$ and $R^4$ are taken together with —OCF$_2$O—, —OCF$_2$CF$_2$—, —CF$_2$CF$_2$O—, or —CH=CHCH=CH—, forming a benzo-fused ring;

provided that when, (a) m and n are 0;

a carbonyl group with methyl carbon (a) is formed,

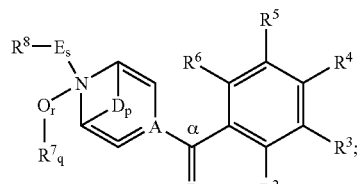

where B is O;

(b) m is 0 and n is 1;

(i) B and $R^1$ are taken together with -G-CH($R^{14}$)—(CH$_2$)$_v$-J-, and with methyl carbon (a), a heterocyclic ring is formed;

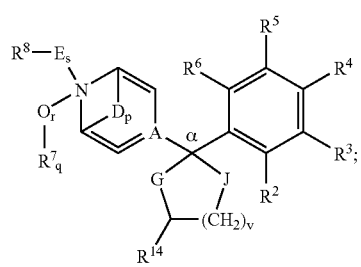

where

G and J are independently selected from O or S; v is 1, or 2; and $R^{14}$ is selected from hydrogen, or aryl optionally substituted with halogen or haloalkyl;

or, ii) A is N, a piperazine ring is formed, and single bonds between methyl carbon (a) and the 4-position of the piperazine ring and to its other substituents are formed;

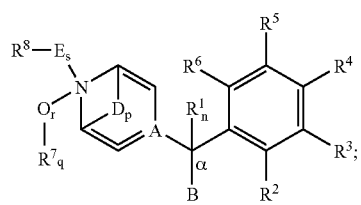

where

B is phenyl substituted with $R^9$, $R^{10}$, $R^{11}$, $R^{12}$, and $R^{13}$,

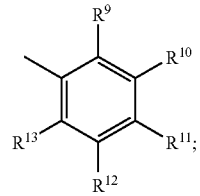

where $R^9$, $R^{10}$, $R^{11}$, $R^{12}$, and $R^{13}$ are independently selected from hydrogen, halogen, alkyl, haloalkyl, hydroxyl, alkoxy, haloalkoxy, mercapto, alkylthio, cyano, alkylcarbonyl, alkoxycarbonyl, and aryloxy, and, wherein either of $R^9$ and $R^{10}$, or $R^{10}$ and $R^{11}$ may be taken together with —OCF$_2$O—, —OCF$_2$CF$_2$—, or —CF$_2$CF$_2$O—, forming a benzo-fused ring;

and, $R^1$ is selected from hydrogen, alkyl, alkoxyalkyl, or aryl;

(c) m is 1 and n is 0;

a double bond between methyl carbon (a) and B is formed;

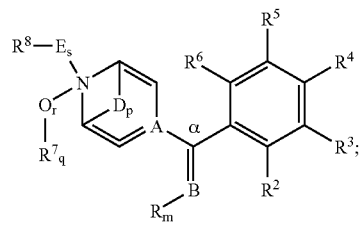

where

B is a bridging group from methyl carbon (a) to R, and is selected from CH—, NN=*, NNR$^{15}$*, NNR$^{15}$CH$_2$*, NNR$^{15}$C(=O)*, NNR$^{15}$SO$_2$*, NNR$^{15}$C(=O)NR$^{16}$* and NNR$^{15}$C(=S)NR$^{16}$* where the asterisk denotes attachment to R;

where $R^{15}$ and $R^{16}$ are independently selected from hydrogen, alkyl, alkylaminocarbonyl, and arylcarbonyl wherein the aryl is optionally substituted with halogen, alkyl, alkoxy, haloalkyl, haloalkoxy, or nitro;

where

R is alkyl, cycloalkyl, alkenyl, or alkoxycarbonyl;

or

R is phenyl substituted with $R^{17}$, $R^{18}$, $R^{19}$, $R^{20}$, and $R^{21}$;

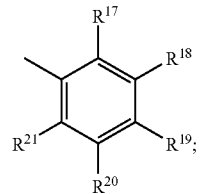

or

R is pyrid-2-yl substituted with $R^{18}$, $R^{19}$, $R^{20}$, and $R^{21}$,

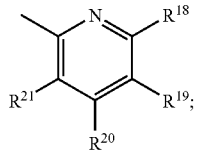

or

R is pyrid-3-yl substituted with $R^{17}$, $R^{19}$, $R^{20}$, and $R^{21}$,

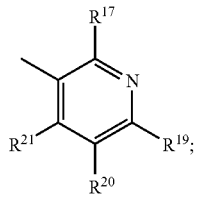

or

R is pyrid-4-yl substituted with $R^{17}$, $R^{18}$, $R^{20}$, and $R^{21}$,

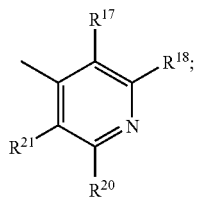

or

R is pyridazin-3-yl substituted with $R^{19}$, $R^{20}$ and $R^{21}$,

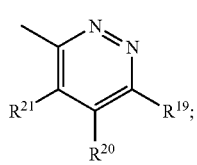

where $R^{17}$, $R^{18}$, $R^{19}$, $R^{20}$, and $R^{21}$ are independently selected from hydrogen, halogen, alkyl, haloalkyl, alkoxy, haloalkoxy, alkylthio, haloalkylthio, cyano, nitro, alkylcarbonyl, alkoxycarbonyl, alkoxycarbonylamino, aryl, aryloxy, or 2-alkyl-2H-tetrazine, and, wherein either of $R^{17}$ and $R^{18}$, or $R^{18}$ and $R^{19}$ may be taken together with —OCF$_2$O—, —OCF$_2$CF$_2$—, —CF$_2$CF$_2$O—, or —CH$_2$CH═CHCH$_2$—, forming a benzo-fused ring;

d) m and n are 1;

A is N, a piperazine ring is formed, and single bonds between methyl carbon (a) and the 4-position of the piperazine ring and to its other substituents are formed;

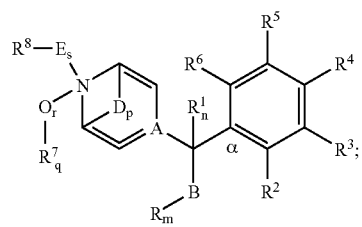

where

B is a bridging group from methyl carbon (a) to R;

where

B is selected from O, S, CH$_2$, *CH$_2$O, *OCH$_2$, OC(═O)O, *OC(═O)NR$^{15}$, *NR$^{15}$C(═O)O, *OC(═S)NR$^{15}$, *NR$^{15}$C(═S)O, *OCH$_2$C(═O)NR$^{15}$, *NR$^{15}$C(═O)CH$_2$O, *CH$_2$C(═O)NR$^{15}$, *NR$^{15}$C(═O)OCH$_2$, *NR$^{15}$CH$_2$, *CH$_2$NR$^{15}$, *NR$^{15}$C(═O), *C(═O)NR$^{15}$, *NR$^{15}$SO$_2$, *SO$_2$NR$^{15}$, *NR$^{15}$NHSO$_2$, *SO$_2$NHNR$^{15}$, *OC(═O)NR$^{15}$SO$_2$, *SO$_2$NR$^{15}$C(═O)O, *OC(═O)NR$^{15}$CHR$^{16}$, *CHR$^{16}$N NR$^{15}$C(═O)O, *NR$^{15}$C(═O)NR$^{16}$; 1,4-dioxycyclohexyl, or 4-oxypiperidin-1-yl, where the asterisk denotes attachment to the methyl carbon (a); where $R^{15}$ and $R^{16}$ are described above;

where

R and $R^1$ are described above;

when p is 1, 2, or 3;

D is —CH$_2$—, and an azabicyclo derivative of the six-membered azine ring is formed;

when q is 0, and r is 1, an N-oxide derivative of the six-membered azine ring nitrogen is formed;

when q is 1 and r is 0 or 1;

$R^7$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate;

when s is 0 or 1;

$R^8$ is selected from hydrogen, alkyl, cycloalkyl, cycloalkylalkyl, alkoxy, alkoxyalkyl, amino, morpholinyl, optionally substituted indolyl. piperidinyl, optionally substituted (pyridyl)alkenyl, optionally substituted 1,2,3,4-tetrahydronaphthylenyl, optionally substituted arylpyrazolyl, benzo[b]thiophenyl, 5-hydropyridino[1,2a]pyrimidinonyl, optionally substituted 4-hydro-1,3-thiazolino[3,2a] pyrimidinonyl, 1,2,3,4-tetrahydroquinolinyl, 2-thioxo-1,3-dihydroquinazolinonyl, 1,3-dihydroquinazolindionyl, or benzo[c]azolindionyl, wherein the optional substituent is selected from halogen, alkyl, alkoxy, and nitro;

or $R^8$ is phenyl substituted with $R^{22}$, $R^{23}$, $R^{24}$, $R^{25}$, and $R^{26}$,

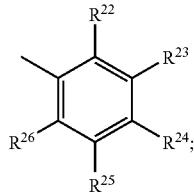

or $R^8$ is pyrid-2-yl substituted with $R^{23}$, $R^{24}$, $R^{25}$, and $R^{26}$,

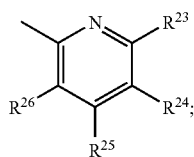

or $R^8$ is pyrid-3-yl substituted with $R^{22}$, $R^{24}$, $R^{25}$, and $R^{26}$,

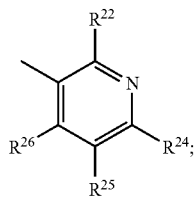

or $R^8$ is pyrid-4-yl substituted with $R^{22}$, $R^{23}$, $R^{25}$, and $R^{26}$,

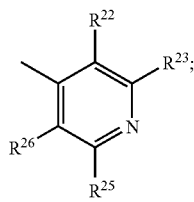

where $R^{22}$, $R^{23}$, $R^{24}$, $R^{25}$, and $R^{26}$ are independently selected from hydrogen, halogen, alkyl, hydroxy, alkoxy, alkoxyalkyl, dialkoxyalkyl, trialkoxyalkyl, alkoxyiminoalkyl, alkenyloxyiminoalkyl, alkynyloxyiminoalkyl, cycloalkylalkoxy, alkoxyalkoxy, alkylthio, dithioalkoxyalkyl, trithioalkoxyalkyl, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, alkenyloxycarbonylamino, alkynyloxycarbonylamino, haloalkylcarbonylamino, alkoxyalkoxycarbonylamino, (alkyl)(alkoxycarbonyl)amino, alkylsulfonylamino, optionally substituted (heteroaryl)(alkoxycarbonyl)amino, optionally substituted arylcarbonylamino, formyl, optionally substituted 1,3-dioxolan-2-yl, optionally substituted 1,3-dioxan-2-yl, optionally substituted 1,3-oxazolidin-2-yl, optionally substituted 1,3-oxazaperhydroin-2-yl, optionally substituted 1,3-dithiolan-2-yl, optionally substituted 1,3-dithian-2-yl, alkoxycarbonyl, alkylaminocarbonyloxy, alkylaminocarbonylamino, dialkylaminocarbonylamino, alkylamino(thiocarbonyl)amino, dialkylphosphoroureidyl, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted heteroaryl, optionally substituted heteroaryloxy, optionally substituted pyrrolyl, optionally substituted pyrazolyl, optionally substituted pyrazinyloxy. optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, dialkoxyalkyl, dithioalkoxyalkyl, cyano, nitro, amino, or alkoxycarbonylamino;

when s is 1;

E is a bridging group selected from —$(CR^{27}R^{28})_x$—$(CR^{29}R^{30})_y$—, —$(CR^{27}R^{28})(CR^{29}R^{30})_y$O—*, —$C_3H_6$—, —$C_4H_8$—, —C(=O)—, —C(=O)$C_2H_4$—*, —$C_2H_4$C(=O)—*, —$C_3H_6$C(=O)—*, —$C_4H_8$NHC(=O)—*, or —C(=S)NH—*, where the asterisk denotes attachment at $R^8$;

where x is 1; y is 0, or 1;

and where $R^{27}$, $R^{28}$, $R^{29}$, and $R^{30}$ are independently selected from hydrogen, alkyl, and aryl optionally substituted with alkoxy;

N-oxides; and agriculturally-acceptable salts thereof;

with the proviso that when

A is N, forming said piperazine ring;

s is 0 or 1; and when s is 1

E is said bridging group C(=O), or —$(CR^{27}R^{28})_x$—$(CR^{29}R^{30})_y$— where x is 1 and y is 0, and $R^{27}$ and $R^{28}$ are hydrogen, and $R^8$ is selected from optionally substituted indolyl, optionally substituted arylpyrazolyl, and benzo[b]thiophenyl;

or, $R^8$ is phenyl substituted with $R^{22}$, $R^{23}$, $R^{24}$, $R^{25}$ and $R^{26}$ where $R^{22}$, $R^{23}$, $R^{25}$ and $R^{26}$ are hydrogen;

and $R^{24}$ is selected from hydrogen, halogen, hydroxy, alkoxy, cycloalkylalkoxy, optionally substituted arylalkoxy, cyano, nitro, alkylamino, alkoxycarbonylamino, (alkyl)(alkoxycarbonyl)amino, (heteroaryl)(alkoxycarbonyl)amino, alkoxycarbonyl, optionally substituted aryloxy, optionally substituted 1,2,5-thiadiazolyloxy, optionally substituted 2H-tetrazole, optionally substituted pyridyl, and optionally substituted pyridyloxy;

then, q is 0, and r is 1, forming an N-oxide.

The present invention is also directed to compositions containing an insecticidally effective amount of at least one of a compound of formula I, and optionally, an effective amount of at least one of a second compound, with at least one agriculturally acceptable extender or adjuvant.

The present invention is also directed to methods of controlling insects, where control is desired, which comprise applying an insecticidally effective amount of the above composition to the locus of crops, or other areas where insects are present or are expected to be present. Other aspects of the present invention will become apparent.

DETAILED DESCRIPTION OF THE INVENTION

One aspect of the present invention relates to certain new and useful compounds, namely certain novel N-(substituted arylmethyl)-4-(disubstituted methyl)piperidine and piperazine derivatives as depicted in general formula I:

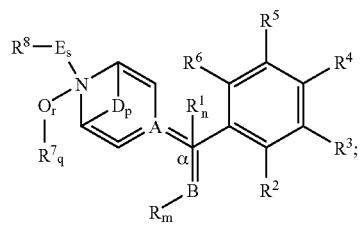

wherein;

m, n, q, r, and s are independently selected from 0 or 1; and p is 0, 1, 2, or 3;

A is CH or N, forming a six-membered azine ring selected from piperidine or piperazine;

$R^2$, $R^3$, $R^4$, $R^5$, and $R^6$ are independently selected from hydrogen, halogen, alkyl, haloalkyl, hydroxyl, alkoxy, haloalkoxy, pentahalothio, alkylthio, cyano, nitro, alkylcarbonyl, alkoxycarbonyl, aryl, or aryloxy, and, wherein either of $R^2$ and $R^3$, or $R^3$ and $R^4$ are taken together with —$OCF_2O$—, —$OCF_2CF_2$—, —$CF_2CF_2O$—, or —CH=CHCH=CH—, forming a benzo-fused ring;

provided that when, (a) m and n are 0;

a carbonyl group with methyl carbon (a) is formed,

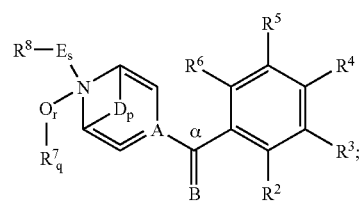

where B is O;

(b) m is 0 and n is 1;

(i) B and $R^1$ are taken together with -G-CH($R^{14}$)—($CH_2$)$_v$-J-, and with methyl carbon (a), a heterocyclic ring is formed;

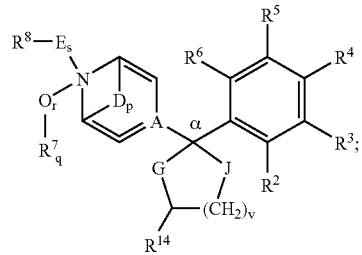

where

G and J are independently selected from O or S; v is 1, or 2; and $R^{14}$ is selected from hydrogen, or aryl optionally substituted with halogen or haloalkyl;

or, ii) A is N, a piperazine ring is formed, and single bonds between methyl carbon (a) and the 4-position of the piperazine ring and to its other substituents are formed;

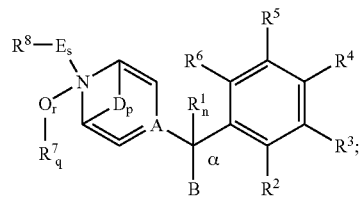

where

B is phenyl substituted with $R^9$, $R^{10}$, $R^{11}$, $R^{12}$, and $R^{13}$,

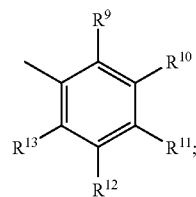

where $R^9$, $R^{10}$, $R^{11}$, $R^{12}$, and $R^{13}$ are independently selected from hydrogen, halogen, alkyl, haloalkyl, hydroxyl, alkoxy, haloalkoxy, mercapto, alkylthio, cyano, alkylcarbonyl, alkoxycarbonyl, and aryloxy, and, wherein either of $R^9$ and $R^{10}$, or $R^{10}$ and $R^{11}$ may be taken together with —$OCF_2O$—, —$OCF_2CF_2$—, or —$CF_2CF_2O$—, forming a benzo-fused ring;

and, $R^1$ is selected from hydrogen, alkyl, alkoxyalkyl, or aryl;

(c) m is 1 and n is 0;

a double bond between methyl carbon (a) and B is formed;

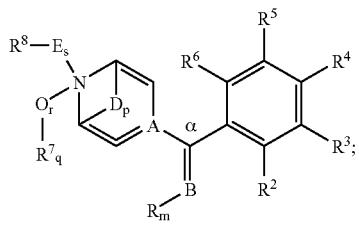

where
B is a bridging group from methyl carbon (a) to R, and is selected from CH—, NN=*, NNR$^{15}$*, NNR$^{15}$CH$_2$*, NNR$^{15}$C(=O)*, NNR$^{15}$SO$_2$*, NNR$^{15}$C(=O)NR$^{16}$* and NNR$^{15}$C(=S)NR$^{16}$* where the asterisk denotes attachment to R;

where
R$^{15}$ and R$^{16}$ are independently selected from hydrogen, alkyl, alkylaminocarbonyl, and arylcarbonyl wherein the aryl is optionally substituted with halogen, alkyl, alkoxy, haloalkyl, haloalkoxy, or nitro;

where
R is alkyl, cycloalkyl, alkenyl, or alkoxycarbonyl;

or
R is phenyl substituted with R$^{17}$, R$^{18}$, R$^{19}$, R$^{20}$ and R$^{21}$;

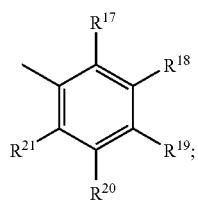

or
R is pyrid-2-yl substituted with R$^{18}$, R$^{19}$, R$^{20}$, and R$^{21}$,

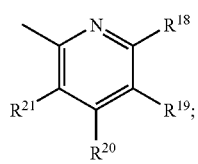

or
R is pyrid-3-yl substituted with R$^{17}$, R$^{19}$, R$^{20}$, and R$^{21}$,

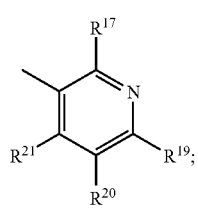

or
R is pyrid-4-yl substituted with R$^{17}$, R$^{18}$, R$^{20}$, and R$^{21}$,

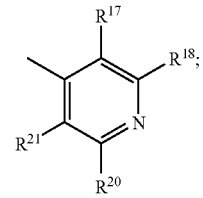

or
R is pyridazin-3-yl substituted with R$^{19}$, R$^{20}$ and R$^{21}$,

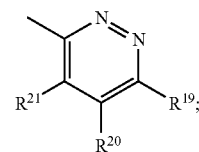

where
R$^{17}$, R$^{18}$, R$^{19}$, R$^{20}$, and R$^{21}$ are independently selected from hydrogen, halogen, alkyl, haloalkyl, alkoxy, haloalkoxy, alkylthio, haloalkylthio, cyano, nitro, alkylcarbonyl, alkoxycarbonyl, alkoxycarbonylamino, aryl, aryloxy, or 2-alkyl-2H-tetrazine, and, wherein either of R$^{17}$ and R$^{18}$, or R$^{18}$ and R$^{19}$ may be taken together with —OCF$_2$O—, —OCF$_2$CF$_2$—, —CF$_2$CF$_2$O—, or —CH$_2$CH=CHCH$_2$—, forming a benzo-fused ring;

d) m and n are 1;
A is N, a piperazine ring is formed, and single bonds between methyl carbon (a) and the 4-position of the piperazine ring and to its other substituents are formed;

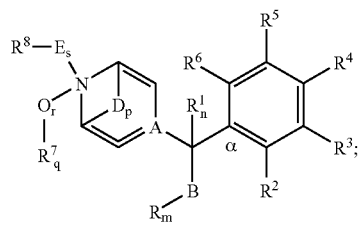

where
B is a bridging group from methyl carbon (a) to R;
where
B is selected from O, S, CH$_2$, *CH$_2$O, *OCH$_2$, OC(=O)O, *OC(=O)NR$^{15}$, *NR$^{15}$C(=O)O, *OC(=S)NR$^{15}$, *NR$^{15}$C(=S)O, *OCH$_2$C(=O)NR$^{15}$, *NR$^{15}$C(=O)CH$_2$O, *CH$_2$OC(=O)NR$^{15}$, *NR$^{15}$C(=O)OCH$_2$, *NR$^{15}$CH$_2$, *CH$_2$NR$^{15}$, *NR$^{15}$C(=O), *C(=O)NR$^{15}$, *NR$^{15}$SO$_2$, *SO$_2$NR$^{15}$, *NR$^{15}$NHSO$_2$, *SO$_2$NHNR$^{15}$, *OC(=O)NR$^{15}$SO$_2$, *SO$_2$NR$^{15}$C(=O)O, *OC(=O)NR$^{15}$CHR$^{16}$, *CHR$^{16}$NR$^{15}$C(=O)O, *NR$^{15}$C(=O)NR$^{16}$; 1,4-dioxycyclohexyl, or 4-oxypiperidin-1-yl, where the asterisk denotes attachment to the methyl carbon (a); where R$^{15}$ and R$^{16}$ are described above;

where
R and R$^1$ are described above;
when p is 1, 2, or 3;

D is —CH$_2$—, and an azabicyclo derivative of the six-membered azine ring is formed;

when q is 0, and r is 1, an N-oxide derivative of the six-membered azine ring nitrogen is formed;

when q is 1 and r is 0 or 1;

R$^7$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate;

when s is 0 or 1;

R$^8$ is selected from hydrogen, alkyl, cycloalkyl, cycloalkylalkyl, alkoxy, alkoxyalkyl, amino, morpholinyl, optionally substituted indolyl. piperidinyl, optionally substituted (pyridyl)alkenyl, optionally substituted 1,2,3,4-tetrahydronaphthylenyl, optionally substituted arylpyrazolyl, benzo[b]thiophenyl, 5-hydropyridino[1,2a]pyrimidinonyl, optionally substituted 4-hydro-1,3-thiazolino[3,2a]pyrimidinonyl, 1,2,3,4-tetrahydroquinolinyl, 2-thioxo-1,3-dihydroquinazolinonyl, 1,3-dihydroquinazolindionyl, or benzo[c]azolindionyl, wherein the optional substituent is selected from halogen, alkyl, alkoxy, and nitro;

or

R$^8$ is phenyl substituted with R$^{22}$, R$^{23}$, R$^{24}$, R$^{25}$, and R$^{26}$,

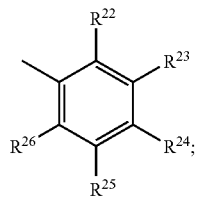

or

R$^8$ is pyrid-2-yl substituted with R$^{23}$, R$^{24}$, R$^{25}$, and R$^{26}$,

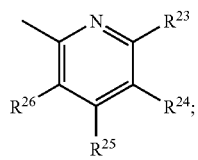

or

R$^8$ is pyrid-3-yl substituted with R$^{22}$, R$^{24}$, R$^{25}$, and R$^{26}$,

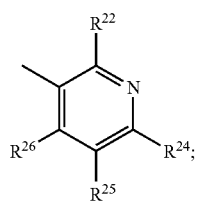

or

R$^8$ is pyrid-4-yl substituted with R$^{22}$, R$^{23}$, R$^{25}$, and R$^{26}$,

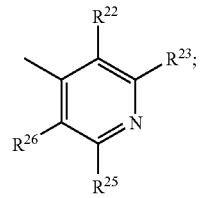

where

R$^{22}$, R$^{23}$, R$^{24}$, R$^{25}$, and R$^{26}$ are independently selected from hydrogen, halogen, alkyl, hydroxy, alkoxy, alkoxyalkyl, dialkoxyalkyl, trialkoxyalkyl, alkoxyiminoalkyl, alkenyloxyiminoalkyl, alkynyloxyiminoalkyl, cycloalkylalkoxy, alkoxyalkoxy, alkylthio, dithioalkoxyalkyl, trithioalkoxyalkyl, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, alkenyloxycarbonylamino, alkynyloxycarbonylamino, haloalkylcarbonylamino, alkoxyalkoxycarbonylamino, (alkyl)(alkoxycarbonyl)amino, alkylsulfonylamino, optionally substituted (heteroaryl)(alkoxycarbonyl)amino, optionally substituted arylcarbonylamino, formyl, optionally substituted 1,3-dioxolan-2-yl, optionally substituted 1,3-dioxan-2-yl, optionally substituted 1,3-oxazolidin-2-yl, optionally substituted 1,3-oxazaperhydroin-2-yl, optionally substituted 1,3-dithiolan-2-yl, optionally substituted 1,3-dithian-2-yl, alkoxycarbonyl, alkylaminocarbonyloxy, alkylaminocarbonylamino, dialkylaminocarbonylamino, alkylamino(thiocarbonyl)amino, dialkylphosphoroureidyl, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted heteroaryl, optionally substituted heteroaryloxy, optionally substituted pyrrolyl, optionally substituted pyrazolyl, optionally substituted pyrazinyloxy. optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahyropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, dialkoxyalkyl, dithioalkoxyalkyl, cyano, nitro, amino, or alkoxycarbonylamino;

when s is 1;

E is a bridging group selected from —(CR$^{27}$R$^{28}$)$_x$—(CR$^{29}$R$^{30}$)$_y$—, —(CR$^{27}$R$^{28}$)$_x$—(CR$^{29}$R$^{30}$)$_y$O—*, —C$_3$H$_6$—, —C$_4$H$_8$—, —C(=O)—, —C(=O)C$_2$H$_4$—*, —C$_2$H$_4$C(=O)—*, —C$_3$H$_6$C(=O)—*, —C$_4$H$_8$NHC(=O)—*, or —C(=S)NH—*, where the asterisk, denotes attachment at R$^8$;

where x is 1; y is 0, or 1;

and where $R^{27}$, $R^{28}$, $R^{29}$, and $R^{30}$ are independently selected from hydrogen, alkyl, and aryl optionally substituted with alkoxy;

N-oxides; and agriculturally-acceptable salts thereof;

with the proviso that when

A is N, forming said piperazine ring;

s is 0 or 1; and when s is 1

E is said bridging group C(=O), or —$(CR^{27}R^{28})_x$—$(CR^{29}R^{30})_y$— where x is 1 and y is 0, and $R^{27}$ and $R^{28}$ are hydrogen, and $R^8$ is selected from optionally substituted indolyl, optionally substituted arylpyrazolyl, and benzo[b]thiophenyl;

or, $R^8$ is phenyl substituted with $R^{22}$, $R^{23}$, $R^{24}$, $R^{25}$ and $R^{26}$ where $R^{22}$, $R^{23}$, $R^{25}$ and $R^{26}$ are hydrogen;

and $R^{24}$ is selected from hydrogen, halogen, hydroxy, alkoxy, cycloalkylalkoxy, optionally substituted arylalkoxy, cyano, nitro, alkylamino, alkoxycarbonylamino, (alkyl)(alkoxycarbonyl)amino, (heteroaryl)(alkoxycarbonyl)amino, alkoxycarbonyl, optionally substituted aryloxy, optionally substituted 1,2,5-thiadiazolyloxy, optionally substituted 2H-tetrazole, optionally substituted pyridyl, and optionally substituted pyridyloxy;

then, q is 0, and r is 1, forming an N-oxide.

Compounds within the scope of the present invention that are of particular interest are those where p and q are 0; r is 0 or 1; and s is 1; $R^2$, $R^3$, $R^4$, $R^5$, and $R^6$ are independently selected from hydrogen, halogen, alkyl, haloalkyl, hydroxyl, alkoxy, haloalkoxy, pentahalothio, alkylthio, nitro, aryl, and aryloxy; E is the bridging group —$(CR^{27}R^{28})_x$—$(CR^{29}R^{30})_y$—, where x is 1 and y is 0, $R^{27}$ and $R^{28}$ are hydrogen; and $R^8$ is phenyl substituted with $R^{22}$, $R^{23}$, $R^{24}$, $R^{25}$, and $R^{26}$, where $R^{22}$, $R^{23}$, $R^{24}$, $R^{25}$, and $R^{26}$ are independently selected from hydrogen, alkoxy, dialkoxyalkyl, dithioalkoxyalkyl, alkoxyiminoalkyl, alkenyloxyiminoalkyl, alkynyloxyiminoalkyl, alkoxycarbonylamino, optionally substituted arylcarbonylamino, alkoxycarbonyl, alkylaminocarbonyloxy, optionally substituted 1,3-dioxolane-2-yl, optionally substituted 1,3-dioxan-2-yl, optionally substituted 1,3-dithiolan-2-yl, optionally substituted 1,3-dithian-2-yl, optionally substituted aryl, optionally substituted aryloxy, optionally substituted 2H-tetrazole, optionally substituted pyridyl, optionally substituted pyridyloxy, optionally substituted pyrimidinyl, optionally substituted pyrimidinyloxy, and optionally substituted pyridazinyloxy.

In one aspect of the present invention, preferred compounds of the present invention are those where A is CH, forming the piperidine ring, m is 0, and (a) n is 0 or (bi) 1;

when (a) m and n are 0, a carbonyl group with methyl carbon (a) is formed; where B is O or (bi) m is 0, and n is 1, B and $R^1$ are taken together with -G-CH($R^{14}$)—$(CH_2)_v$-J- and with methyl carbon (a) a heterocyclic ring is formed, where $R^{14}$ is hydrogen;

where $R^2$, $R^3$, $R^4$, $R^5$, and $R^6$ are independently selected from hydrogen, halogen, haloalkyl, and haloalkoxy;

and $R^{22}$, $R^{23}$, $R^{24}$, $R^{25}$, and $R^{26}$ are independently selected from hydrogen, dialkoxyalkyl, dithioalkoxyalkyl, alkoxyiminoalkyl, alkylaminocarbonyloxy, optionally substituted 1,3-dioxolan-2-yl, optionally substituted 1,3-dioxan-2-yl, optionally substituted aryloxy, optionally substituted 2H-tetrazole, optionally substituted pyridyloxy, optionally substituted pyrimidinyl, optionally substituted pyrimidinyloxy, and optionally substituted pyridazinyloxy.

More preferred are those compounds where $R^2$, $R^3$, $R^5$, $R^6$, $R^{22}$, $R^{23}$, $R^{25}$, and $R^{26}$ are hydrogen; $R^4$ is difluoromethyl, trifluoromethyl or trifluoromethoxy; and $R^{24}$ is pyrid-2-yloxy or pyrimidin-2-yloxy; and particularly preferred are those where (a) m and n are 0, and a carbonyl group with methyl carbon (a) is formed, where B is O.

In another aspect of the present invention, preferred compounds of the present invention are those where A is CH, forming the piperidine ring;

where (c) m is 1, and n is 0, a double bond between methyl carbon (a) and B is formed, where B is a bridging group from methyl carbon (a) to R;

where

B is selected from CH, $NNR^{15}$*, $NNR^{15}C(=O)$*, $NNR^{15}SO_2$*, $NNR^{15}C(=O)NR^{16}$* and $NNR^{15}C(=S)R^{16}$*, where $R^{15}$ and $R^{16}$ are hydrogen;

and

R is phenyl substituted with $R^{17}$, $R^{18}$, $R^{19}$, $R^{20}$, and $R^{21}$ where $R^{17}$, $R^{18}$, $R^{19}$, $R^{20}$, and $R^{21}$ are independently selected from hydrogen, halogen, alkyl, haloalkyl, alkoxy, haloalkoxy, nitro, aryl, aryloxy, and 2-alkyl-2H-tetrazole.

More preferred are those compounds where $R^2$, $R^3$, $R^4$, $R^5$, and $R^6$ are independently selected from hydrogen, halogen, haloalkyl, and haloalkoxy; and $R^{22}$, $R^{23}$, $R^{24}$, $R^{25}$, and $R^{26}$ are independently selected from hydrogen, dialkoxyalkyl, dithioalkoxyalkyl, alkoxyiminoalkyl, alkylaminocarbonyloxy, optionally substituted 1,3-dioxolan-2-yl, optionally substituted 1,3-dioxan-2-yl, optionally substituted aryloxy, optionally substituted 2H-tetrazole, optionally substituted pyridyloxy, optionally substituted pyrimidinyl, optionally substituted pyrimidinyloxy, and optionally substituted pyridazinyloxy.

Particularly preferred are those compounds where B is the bridging group $NNR^{15}C(=O)$*, $NNR^{15}SO_2$*, or $NNR^{15}C(=O)NR^{16}$*; and $R^{17}$, $R^{18}$, $R^{19}$, $R^{20}$, and $R^{21}$ are independently selected from hydrogen, halogen, haloalkyl, and haloalkoxy; more particularly where $R^2$, $R^3$, $R^5$, $R^6$, $R^{17}$, $R^{18}$, $R^{20}$, $R^{21}$, $R^{22}$, $R^{23}$, $R^{25}$, and $R^{26}$ are hydrogen; $R^4$ and $R^{19}$ are difluoromethyl, trifluoromethyl or trifluoromethoxy; and $R^{24}$ is pyrid-2-yloxy or pyrimidin-2-yloxy.

In yet another aspect of the present invention, preferred compounds of the present invention are those where A is N, forming the piperazine ring, bii) m is 0 or d) 1, and n is 1;

when bii) m is 0 and n is 1;

single bonds between methyl carbon (a) and the 4-position of said piperazine ring and its other substituents are formed;

where

B is phenyl substituted with $R^9$, $R^{10}$, $R^{11}$, $R^{12}$, and $R^{13}$, where $R^9$, $R^{10}$, $R^{11}$, $R^{12}$, and $R^{13}$ are independently selected from hydrogen, halogen, alkyl, haloalkyl, hydroxyl, alkoxy, haloalkoxy, mercapto, and alkylthio;

and $R^1$ is hydrogen;

or d) m and n are 1;

B is said bridging group selected from $CH_2$, $*CH_2O$, $*CH_2C(=O)NR^{15}$, $*CH_2NR^{15}$, and $*C(=O)NR^{15}$, where $R^{15}$ and $R^{16}$ are hydrogen;

and

R is phenyl substituted with $R^{17}$, $R^{18}$, $R^{19}$, $R^{20}$, and $R^{21}$ where $R^{17}$, $R^{18}$, $R^{19}$, $R^{20}$, and $R^{21}$ are independently selected from hydrogen, halogen, alkyl, haloalkyl, alkoxy, haloalkoxy, nitro, aryl, aryloxy, and 2-alkyl-2H-tetrazole.

More preferred are those compounds where $R^2$, $R^3$, $R^4$, $R^5$, and $R^6$ are independently selected from hydrogen, halogen, haloalkyl, and haloalkoxy; and $R^{22}$, $R^{23}$, $R^{24}$, $R^{25}$, and $R^{26}$ are independently selected from hydrogen, dialkoxyalkyl, dithioalkoxyalkyl, alkoxyiminoalkyl, alkylaminocarbonyloxy, optionally substituted 1,3-dioxolan-2-yl, optionally substituted 1,3-dioxan-2-yl, optionally substituted aryloxy, optionally substituted 2H-tetrazole, optionally substituted pyridyloxy, optionally substituted pyrimidinyl, optionally substituted pyrimidinyloxy, and optionally substituted pyridazinyloxy.

Particularly preferred are those compounds where bii) m is 0 and n is 1, and $R^9$, $R^{10}$, $R^{11}$, $R^{12}$, and $R^{13}$ are independently selected from hydrogen, halogen, haloalkyl, and haloalkoxy; more particularly where $R^2$, $R^3$, $R^5$, $R^6$, $R^9$, $R^{10}$, $R^{12}$, $R^{13}$, $R^{22}$, $R^{23}$, $R^{25}$, and $R^{26}$ are hydrogen; $R^4$ and $R^{11}$ are difluoromethyl, trifluoromethyl or trifluoromethoxy; and $R^{24}$ is pyrid-2-yloxy or pyrimidin-2-yloxy.

Other particularly preferred are those compounds where d) m and n are 1; B is the bridging group $CH_2$, or $*CH_2O$; and $R^{17}$, $R^{18}$, $R^{19}$, $R^{20}$, and $R^{21}$ are independently selected from hydrogen, halogen, haloalkyl, and haloalkoxy; more particularly where $R^2$, $R^3$, $R^5$, $R^6$, $R^{17}$, $R^{18}$, $R^{20}$, $R^{21}$, $R^{22}$, $R^{23}$, $R^{25}$, and $R^{26}$ are hydrogen; $R^4$ and $R^{19}$ are difluoromethyl, trifluoromethyl or trifluoromethoxy; and $R^{24}$ is pyrid-2-yloxy or pyrimidin-2-yloxy.

In certain cases the compounds within the scope of formula I may possess asymmetric centers, which can give rise to optical enantiomorphs and diastereomers. Compounds within the scope of formula I may exist in two or more forms, i.e., polymorphs, which are significantly different in physical and chemical properties. Compounds within the scope of formula I may also exist as tautomers, which are in equilibrium. Compounds within the scope of formula I may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I, and, optionally, an effective amount of at least one second compound, with at least one agriculturally acceptable extender or adjuvant.

Another aspect of the present invention relates to methods of controlling insects by applying an insecticidally effective amount of a composition set forth above to a locus of crops such as, without limitation, cereals, cotton, vegetables, and fruits, other areas where insects are present or are expected to be present, or adjacent to areas where insects are present or are expected to be present.

The present invention also includes the use of the compounds and compositions set forth herein for control of non-agricultural insect species, for example, ants, dry wood termites and subterranean termites as well as other insects; and also for use as pharmaceutical agents and compositions thereof.

In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* sp., *Rhodnius* spp., *Ctenocephalides canis*, and other species.

As used in this specification and unless otherwise indicated the substituent terms "alkyl", "alkenyl", "alkynyl", "alkoxy", "alkenyloxy", and "alkynyloxy" used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms, wherein "alkenyl" has at least one carbon to carbon double bond, and "alkynyl" has at least one carbon to carbon triple bond. The term "aryl" refers to an aromatic ring structure, including fused rings, having four to ten carbon atoms, for example, phenyl and naphthyl. The term "heteroaryl" refers to an aromatic ring structure, including fused rings, having four to ten carbon atoms, and in which one or more of the atoms in the ring is other than carbon, for example, sulfur, oxygen, or nitrogen. The term "THF" refers to tetrahydrofuran. The term "DMSO" refers to methyl sulfoxide. The term "DMF" refers to N,N-dimethylformamide. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C.

The compounds of formula I of the present invention can be synthesized by methods that are individually known to one skilled in the art from intermediate compounds readily available in commerce.

Scheme 1 below illustrates a general procedure for synthesizing those compounds of formula I, where A is CH, forming a piperidine ring; m and n are 0, forming a carbonyl group with the methyl carbon (a), where B is O; and p, q, and s are 0:

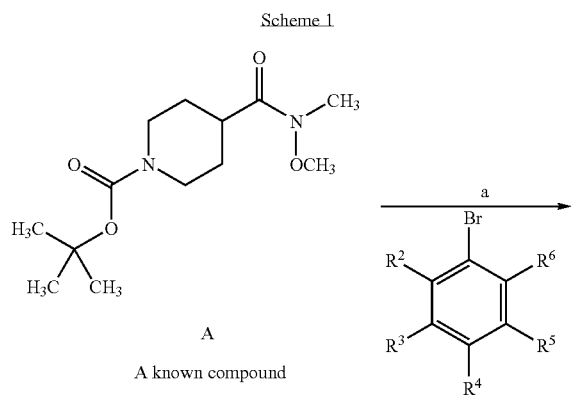

ecarboxylate (A), yielding, the corresponding alkyl(4-substituted phenyl)carbonylpiperidinecarboxylate, for example, tert.-butyl 4-{4-(trifluoromethyl)phenyl]carbonyl}piperidinecarboxylate (B). Then, the protecting group was cleaved from intermediate (B) using trifluoroacetic acid, affording the corresponding compound of formula I, for example, 4-piperidyl 4-(trifluoromethyl)phenyl ketone. Example 1, set forth below provides a detailed procedure for this synthesis.

Scheme 2 below illustrates a general procedure for synthesizing those compounds of formula I where A is CH, forming a piperidine ring; n is 0, forming a double bond from the methyl carbon (a) to B, where B is a bridging group from the methyl carbon to R; p, q, and r are 0; m and s are 1; E is $-(CR^{27}R^{28})_x-(CR^{29}R^{30})_y-$, where x is 1, and y is 0; $R^8$ is phenyl substituted with $R^{22}$, $R^{23}$, $R^{24}$, $R^{25}$, and $R^{26}$; and R is phenyl substituted with $R^{17}$, $R^{18}$ $R^{19}$, $R^{20}$, and $R^{21}$; where $R^{27}$, and $R^{28}$ are hydrogen:

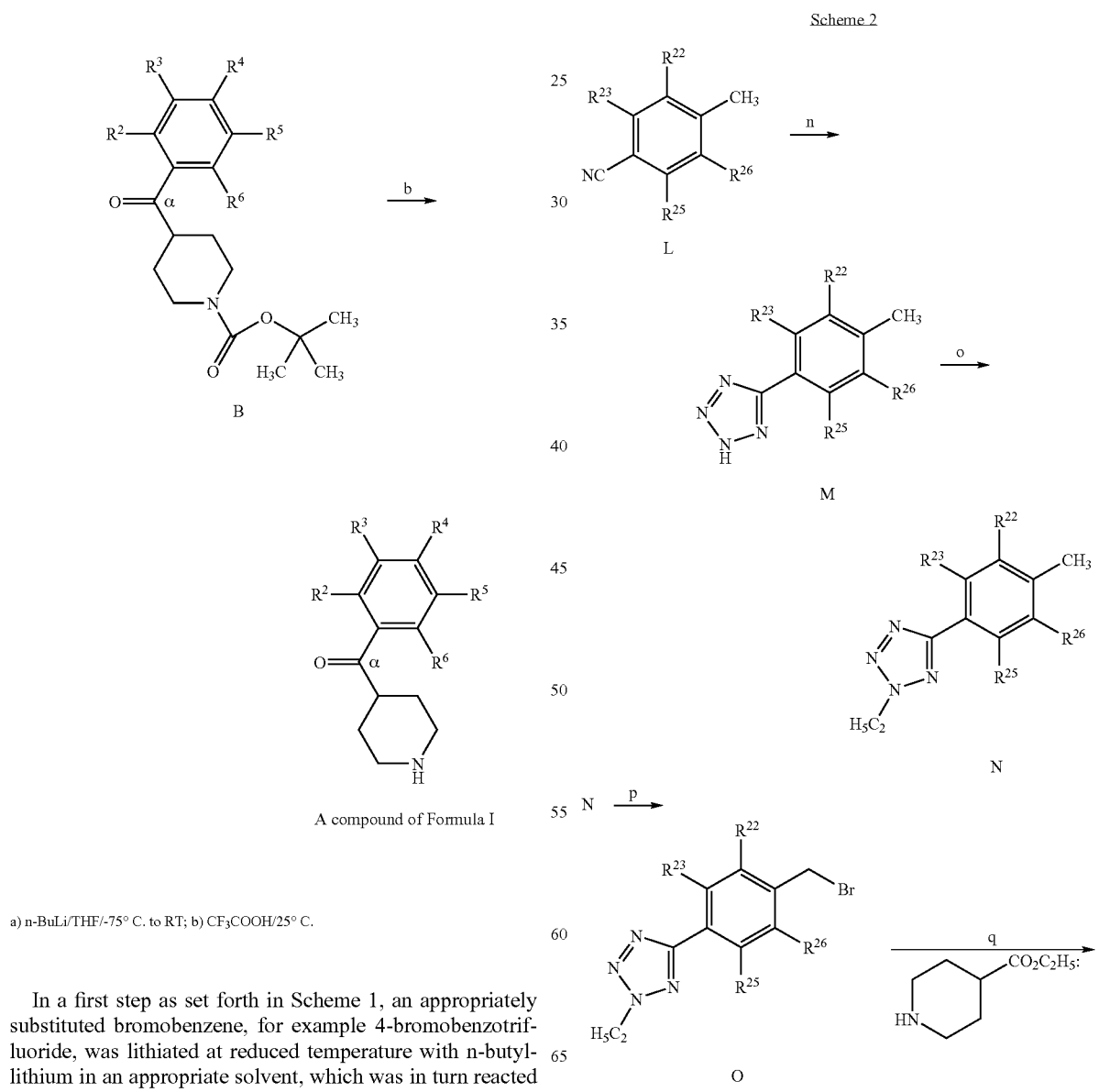

a) n-BuLi/THF/-75° C. to RT; b) CF$_3$COOH/25° C.

In a first step as set forth in Scheme 1, an appropriately substituted bromobenzene, for example 4-bromobenzotrifluoride, was lithiated at reduced temperature with n-butyllithium in an appropriate solvent, which was in turn reacted with an alkyl 4-(N-methoxy-N-methylcarbamoyl)piperidin-

27

-continued

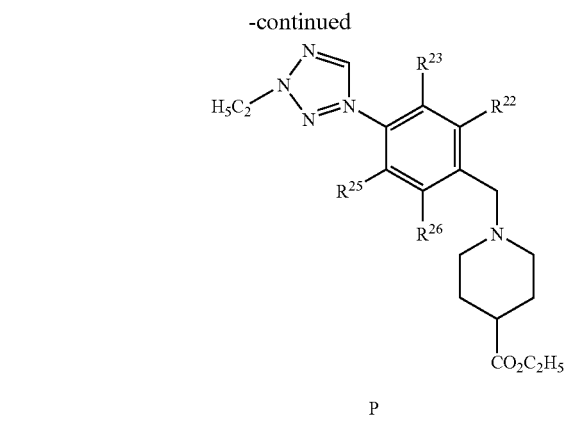

P

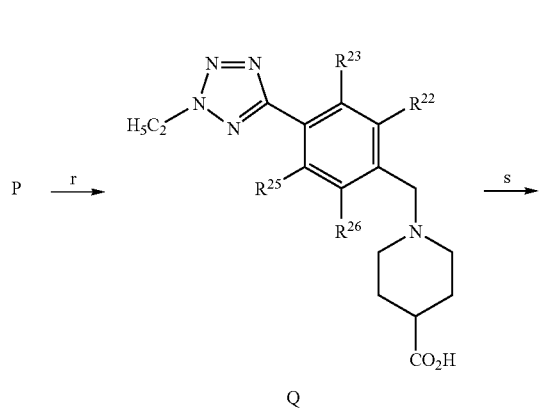

Q

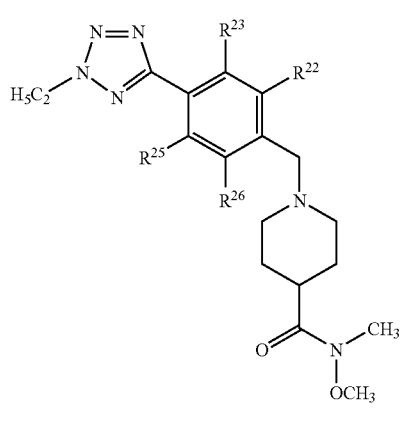

R

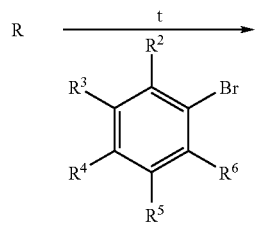

28

-continued

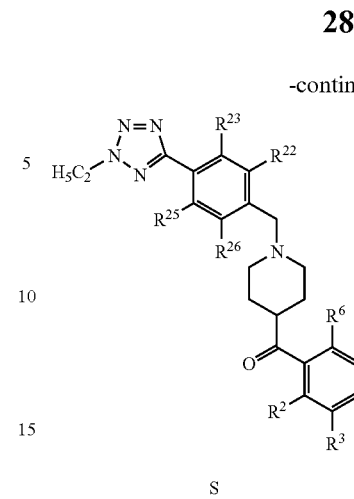

S

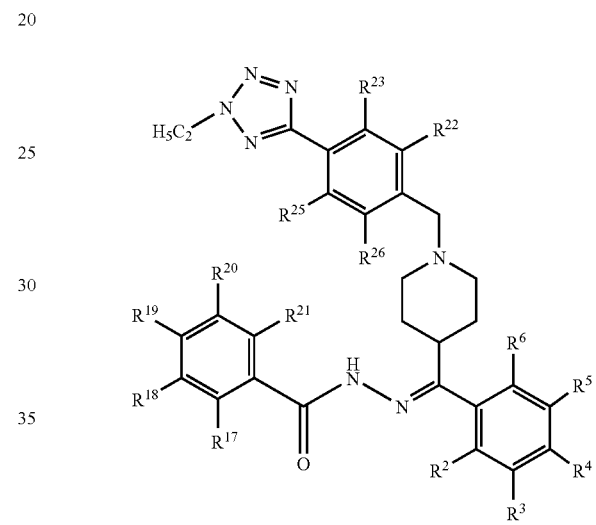

A compound of formula I n) NaN₃/NH₄Cl/DMF/140° C.; o)EtI/K₂CO₃/DMF;
p) NBS/CCl₄/Reflux;
q) N,N-diisopropylethylamine/DMSO;r) NaOH/H₂O/MeOH/THF;
s) (EtO)₂P(O)CN/HN(OCH₃)(CH₃):HCl/DMF/0° C.;
t) Mg/THF/R,T-70° C.;
u)EtOH/100° C.

As depicted in Scheme 2, Intermediate (M), for example, 5-(4-methylphenyl)-1,2,3,4-tetraazole, was prepared by reacting an appropriate toluonitrile, for example para-toluonitrile, with sodium azide at elevated temperature in an appropriate solvent. Intermediate (M) was then alkylated with an appropriate iodoalkane under basic conditions, affording the corresponding alkylated tetraazole (N), for example, 2-ethyl-5-(4-methylphenyl)-1,2,3,4-tetraazole. Intermediate (N) was in turn brominated with, for example, N-bromosuccinimide at elevated temperature in an appropriate solvent, providing the corresponding bromomethyl derivative (O), for example, 5-[4-(bromomethyl)phenyl]-2-ethyl-1,2,3,4-tetraazole. Intermediate (O) was then reacted with ethyl isonipecotate under basic conditions in an appropriate solvent, providing the corresponding ester (P), for example, ethyl 1-{[4-(2-ethyl-1,2,3,4-tetraazol-5-yl)phenyl)methyl}piperidine-4-carboxylate, which was in turn converted to its piperidinecarboxylic acid (Q) by reacting it with aqueous sodium hydroxide in an appropriate solvent, affording, for example, 1-{[4-(2-ethyl-1,2,3,4-tetraazol-5-yl)phenyl]methyl}piperidinecarboxylic acid. Intermediate (Q) was then reacted with, for example, N,O-dimethylhydroxylamine hydrochloride and diethylcyanophosphonate, under basic conditions at reduced temperature in an appropriate solvent, yielding the corresponding piperidine carboxamine (R), for example, 1-{[4-(2-ethyl(1,2,3,4-tetraazol-5-yl))phenyl]methyl}4-piperidyl)-N-methoxy-N-methylcarboxamide. Intermediate (R) was reacted with a Grignard Reagent, for example, 4-trifluoromethoxyphenylmagnesium bromide, in an appropriate solvent, affording the corresponding ketone (S), for example, 1-{[4-(2-ethyl(1,2,3,4-tetraazol-5-yl))phenyl]methyl}(4-piperidyl)-4-(trifluoromethoxy)phenyl ketone. The ketone (S) was then reacted with, for example, an appropriate benzoic acid hydrazide, such as 4-(trifluoromethoxy)benzoic acid hydrazide, at elevated temperature in an appropriate solvent, providing the corresponding carboxamide, a compound of formula I, for example, N-[1-aza-2-(1-{[4-(2-ethyl(1,2,3,4-tetraazol-5-yl))phenyl]methyl}4-piperidyl))-2-[4-(trifluoromethoxy)phenyl]vinyl][4-(trifluoromethoxy)phenyl]carboxamide.

Example 2, set forth below provides a detailed procedure for this synthesis.

Scheme 3 below illustrates a general procedure for synthesizing those compounds of formula I where A is CH, forming a piperidine ring; p, q, r and m are 0; n and s are 1; where B and $R^1$ are taken together with -G-CH($R^{14}$)—($CH_2$)$_v$ -J-, and with the methyl carbon (a), form a heterocyclic derivative; E is —($CR^{27}R^{28}$)$_x$—($CR^{29}R^{30}$)$_y$—, where x is 1, and y is 0; and $R^8$ is phenyl substituted with $R^{22}$, $R^{23}$, $R^{24}$, $R^{25}$, and $R^{26}$; where $R^2$, $R^3$, $R^5$, $R^6$, $R^{22}$, $R^{23}$, $R^{25}$, $R^{26}$, $R^{27}$ and $R^{28}$ are hydrogen:

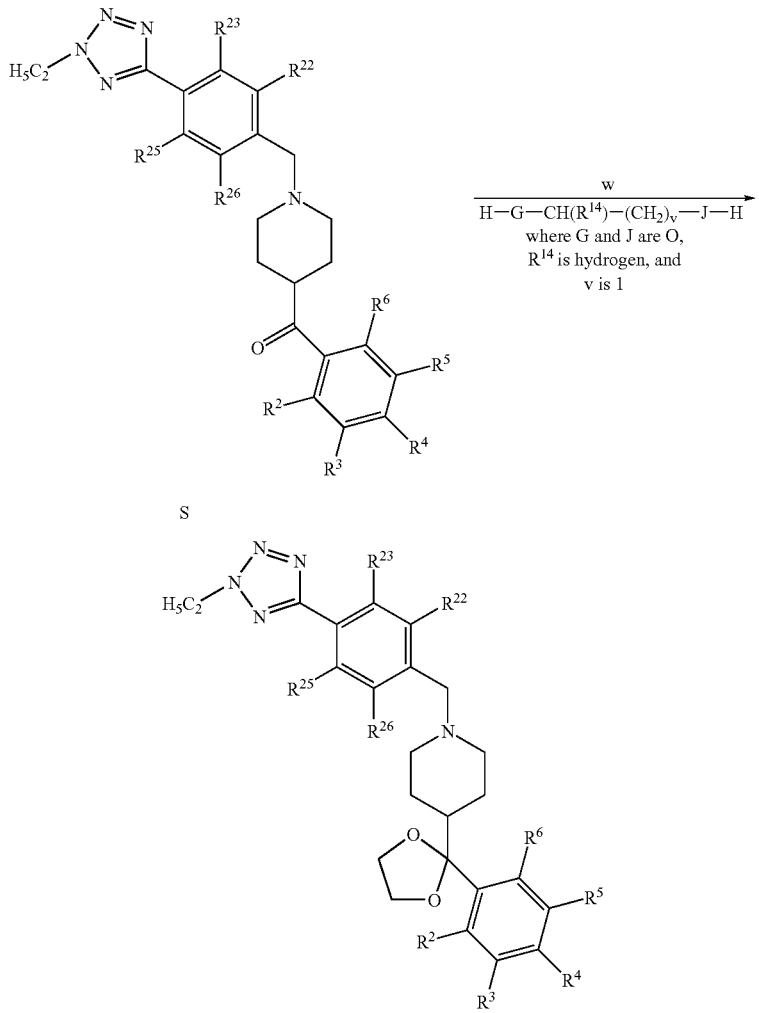

w) p-toluenesulfonic acid/Toluene/Reflux

As depicted in Scheme 3, Intermediate (S), for example, 1-{[4-(2-ethyl(1,2,3,4-tetraazol-5-yl))phenyl]methyl}4-piperidyl)-4-(trifluoromethoxy)phenyl ketone, as set forth in Scheme 2, is converted to its ketal by reacting it with for example, ethylene glycol in the presence of a catalyst, yielding a compound of formula I where B and $R^1$ are taken together with -G-CH($R^{14}$)—(CH$_2$)$_v$-J-, and with the methyl carbon (a), form a heterocyclic derivative. Example 5, set forth below provides a detailed procedure for this synthesis.

Scheme 4 below illustrates another general procedure for synthesizing those compounds of formula I where A is N, forming a piperazine ring; n is 1, forming single bonds from the methyl carbon and its substituents; p, q, r, and m are 0, s is 1; E is —(CR$^{27}$R$^{28}$)$_x$—(CR$^{29}$R$^{30}$)$_y$—, where x is 1, and y is 0; B is phenyl substituted with $R^9$, $R^{10}$, $R^{11}$, $R^{12}$, and $R^{13}$; and $R^8$ is phenyl substituted with $R^{22}$, $R^{23}$, $R^{24}$, $R^{25}$, and $R^{26}$; where $R^1$, $R^2$, $R^3$, $R^5$, $R^6$, $R^9$, $R^{10}$, $R^{12}$, $R^{13}$, $R^{22}$, $R^{23}$, $R^{25}$, $R^{26}$, $R^{27}$, and $R^{28}$ are hydrogen:

1-oxide (q is 0 and r is 1), for example, 2-{4-[(4-{bis[4-(trifluoromethyl)phenyl]methyl}1-oxypiperazinyl)methyl]phenoxy}pyrimidine, another compound of formula I. Examples 3 and 4, set forth below provide a detailed procedure for these syntheses.

Scheme 5 below illustrates another general procedure for synthesizing those compounds of formula I where A is N, forming a piperazine ring; n is 1, forming single bonds from the methyl carbon and its substituents; p and q are 0; m, r and s are 1; B is a bridging group from the methyl carbon (a) to R; E is —(CR$^{27}$R$^{28}$)$_x$—(CR$^{29}$R$^{30}$)$_y$—, where x is 1, and y is 0; $R^8$ is phenyl substituted with $R^{22}$, $R^{23}$, $R^{24}$, $R^{25}$, and $R^{26}$; and R is phenyl substituted with $R^{17}$, $R^{18}$, $R^{19}$, $R^{20}$, and $R^{21}$; where $R^1$, $R^2$, $R^3$, $R^5$, $R^6$, $R^{21}$, $R^{22}$, $R^{23}$, $R^{25}$, $R^{26}$, $R^{27}$ and $R^{28}$ are hydrogen:

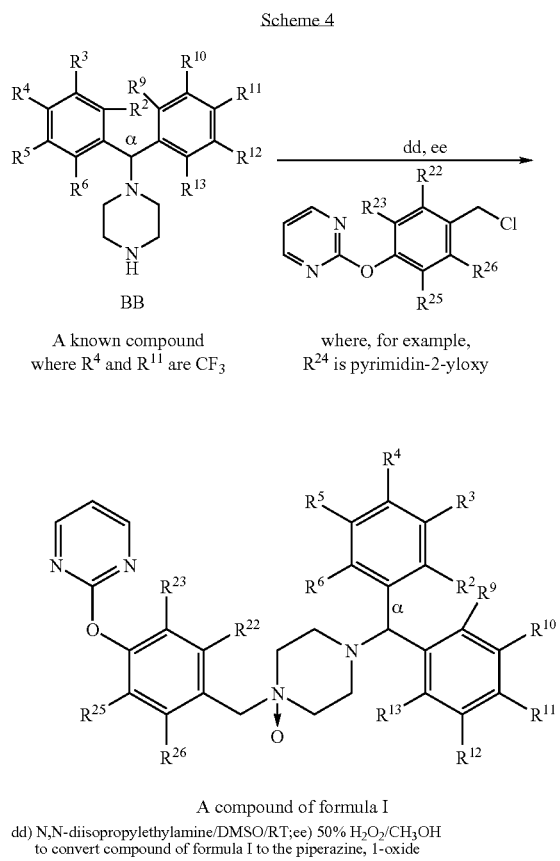

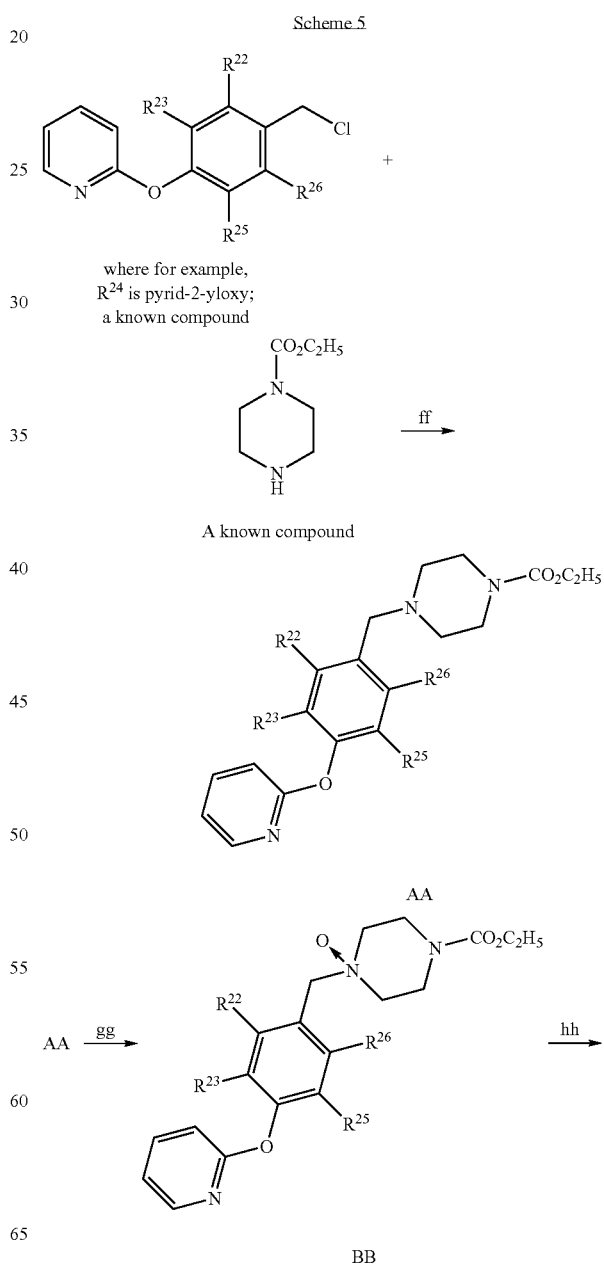

As depicted in Scheme 4, the known piperazine intermediate (BB), for example, {bis[4-(trifluoromethyl)phenyl]methyl}piperazine, was reacted with an appropriate alkyl halide, for example, 2-[4-(chloromethyl)phenoxy]pyrimidine, under basic conditions in an appropriate solvent, affording a piperazine derivative, for example, 2-{4-[(4-{bis[4-(trifluoromethyl)phenyl]methyl}piperazinyl)methyl]phenoxy}pyrimidine, a compound of formula I. Optionally, the so-prepared piperazine derivative I may be treated with an oxidizing agent, such as 50% hydrogen peroxide, in an appropriates solvent, yielding the corresponding piperazin-

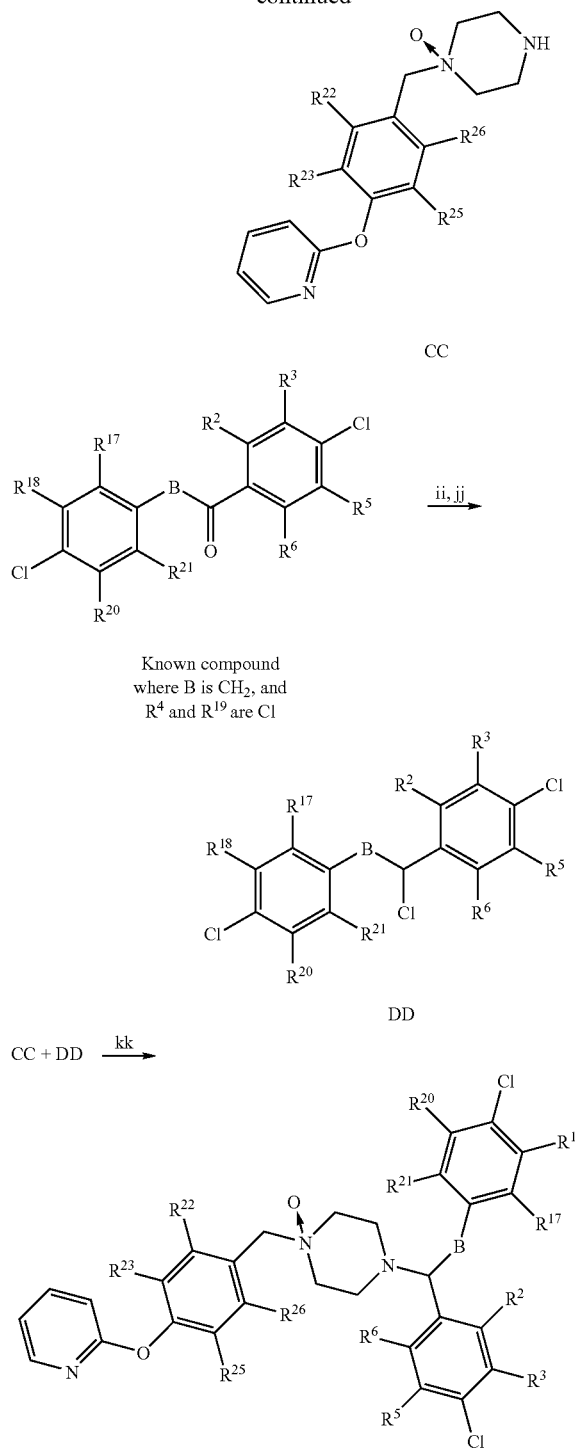

ff) diisopropylethylamine/DMSO/RT; gg) 30% H₂O₂/CH₃OH/RT; hh) 50% NaOH/1:1 THF—CH₃OH/ 80° C.; ii) NaBH4/CH3OH/RT; jj) SOCl₂//pyridine (cat.)/toluene/reflux; kk) diisopropylethylamine/DMSO/RT As depicted in Scheme 5, the known piperazine intermediate, for example, ethyl 1-piperazinecarboxylate (2000-2001 Aldrich Chemical catalog, pg 795), was reacted with the known methyl halide, for example 4-(2-pyridyloxy) phenylmethyl chloride (WO 97/26252) under basic conditions in an appropriate solvent, affording the corresponding ethyl ester, ethyl 4-[(4-(2-pyridyloxy)phenyl)methyl]piperazinecarboxylate (AA). Intermediate (AA) was then oxidized with, for example 30% hydrogen peroxide, providing the corresponding 4-oxide, ethyl 4-[(4-(2-pyridyloxy)phenyl) methyl]-4-oxypiperazinecarboxylate (BB), which in turn was decarboxylated with a strong aqueous base, providing the corresponding free piperazine 4-oxide, for example 2-[4-(4-oxypiperazin-1-ylmethyl)phenoxy]pyridine (CC).

A second intermediate (DD), for example 4-chloro-1-[2-chloro-2-(4-chlorophenyl)ethyl]benzene, for reaction with Intermediate (CC) is prepared by first treating 1,2-di(4-chlorophenyl)ethan-1-one (commercially available) with a reducing agent such as sodium borohydride, to provide the corresponding alcohol 1,2-bis(4-chlorophenyl)ethan-1-ol, then halogenating the so-prepared alcohol with, for example thionyl chloride in the presence of a base such as pyridine, affording the corresponding chloro derivative, Intermediate (DD).

Intermediate (DD) is then reacted with the free piperazine 4-oxide Intermediate (CC) under basic conditions, affording the corresponding compound of formula I, for example 2-[4-({4-[1,2-bis(4-chlorophenyl)ethyl]-1-oxypiperazinyl}methyl)phenoxy]pyridine. Example 6, set forth below provides a detailed procedure for these syntheses.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized, sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4-chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]amino]sulfonyl]-1-methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]

benzenesulfonamide ("triasulfuron"); 2-(4-aryloxyphenoxy) alkanoic acids such as (+/−)-2[4-[(6-chloro-2-benzoxazolyl) oxy]phenoxy]propanoic acid (fenoxaprop"), (+/−)-2-[4[[5-(trifluoromethyl)-2-pyridinyl]oxy]phenoxy]propanoic acid ("fluazifop"), (+/−)-2-[4-(6-chloro-2-quinoxalinyl)oxy]phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, biphenthrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazine fungicides, such as benomyl, carbendazim, thiabendazine, and thiophanate-methyl; 1,2,4-triazine fungicides, such as epoxyconazine, cyproconazine, flusilazine, flutriafol, propiconazine, tebuconazine, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazine, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldecarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This Example Illustrates One Protocol for the Preparation of 4-piperidyl 4-(trfluoromethyl)phenyl ketone (Compound 3 in Table Below)

Step A Synthesis of tert.-butyl 4-{4-(trifluoromethyl)phenyl]carbonyl}piperidinecarboxylate as an Intermediate A stirred solution of 3.0 grams (0.013 mole) of 4-bromobenzotrifluoride in 60 mL of dry THF was cooled to −75° C. and 5.4 mL (0.013 mole) of n-butyllithium (2.5M in hexane) was added. Upon completion of addition, the reaction mixture was stirred at −75° C. for 20 minutes, then a solution of 2.7 grams (0.010 mole) of tert.-butyl 4-(N-methoxy-N-methylcarbamoyl)piperidinecarboxylate (a known compound) in 70 mL of THF was added slowly. Upon completion of addition, the reaction mixture was allowed to warm to 25° C., where it stirred for about 18 hours. The reaction mixture was then poured into ice-water, and the mixture was extracted with diethyl ether. The extract was dried with magnesium sulfate, filtered, and the filtrate was concentrated under reduced pressure to a residue. The residue was purified with column chromatography on silica gel using methylene chloride as eluant. The appropriate fractions were combined and concentrated under reduced pressure, yielding 0.35 gram of the subject compound, mp 84-85° C. The synthesis was repeated.

Step B Synthesis of Compound 3

Tert.-butyl 4-{4-(trifluoromethyl)phenyl]carbonyl}piperidinecarboxylate, 1.4 grams (0.004 mole), in 10 mL of trifluoroacetic acid was stirred at 25° C. for about 18 hours. After this time, the solution was poured into ice-water, then it was made basic to pH of 8 with aqueous 50% sodium hydroxide solution. The mixture was extracted with diethyl ether, and the extract was dried with magnesium sulfate and filtered. The filtrated was concentrated under reduced pressure, yielding 0.6 gram of Compound 3, mp 72-74° C. The NMR spectrum was consistent with the proposed structure.

EXAMPLE 2

This Example Illustrates One Protocol for the Preparation of N-[1-aza-2-(1-{[4-(2-ethyl(1,2,3,4-tetraazol-5-yl))phenyl]methyl}(4-piperidyl))-2-[4-(trifluoromethoxy)phenyl]vinyl][4-(trifluoromethoxy)phenyl]carboxamide (Compound 149 in Table Below)

Step A Synthesis of 5-(4-methylphenyl)-1,2,3,4-tetraazole as an Intermediate

A solution of 10.0 grams (0.085 mole) of para-toluonitrile in 160 mL of DMF was stirred and 5.6 grams (0.085 mole) of sodium azide was added. Upon completion of addition, the reaction mixture was warmed to 135° C. where it stirred for three hours. The reaction mixture was then cooled and poured into 200 mL of stirred, cold aqueous 1N hydrochloric acid. Upon completion of addition, the mixture was stirred for five minutes and filtered to collect a white solid. The solid was dried for 16 hours in a vacuum oven at 35-40° C., yielding 7.1 grams of the subject compound. The reaction was repeated.

Step B Synthesis of 2-ethyl-5-(4-methylphenyl)-1,2,3,4-tetraazole as an Intermediate A solution of 20.0 grams (0.125 mole) of 5-(4-methylphenyl)-1,2,3,4-tetraazole in 230 mL of acetonitrile was stirred and 48.7 grams (0.312 mole) of iodoethane, followed by 17.3 grams (0.125 mole) of potassium carbonate were added. Upon completion of addition, the reaction mixture was warmed to reflux, where it stirred for two hours. After this time, the reaction mixture was concentrated under reduced pressure to a residue. The residue was taken up in ethyl acetate and filtered. The filtrate was concentrated under reduced pressure to a residue. The residue was purified with column chromatography on silica gel using 1:4 ethyl acetate: hexane as an eluant. The appropriate fractions were combined and concentrated under reduced pressure, yielding 18.8 grams of the subject compound. The NMR spectrum was consistent with the proposed structure.

Step C Synthesis of 5-[4-(bromomethyl)phenyl]-2-ethyl-1,2,3,4-tetraazole as an Intermediate A solution of 18.8 grams (0.100 mole) of 2-ethyl-5-(4-methylphenyl)-1,2,3,4-tetraazole in 156 mL of carbon tetrachloride was stirred, and 19.6 grams (0.110 mole) of N-bromosuccinimide, followed by 0.24 gram (0.001 mole) of benzoyl peroxide were added. Upon completion of addition, the reaction mixture was heated to reflux where it stirred for 90 minutes. After this time the reaction mixture was cooled and filtered. The filtrate was concentrated under reduced pressure, yielding 27.7 grams of the subject compound. The NMR spectrum was consistent with the proposed structure.

Step D Synthesis of ethyl 1-{[4-(2-ethyl-1,2,3,4-tetraazol-5-yl)phenyl]methyl}piperidine-4-carboxylate as an Intermediate A solution of 16.0 grams (0.102 mole) of ethyl isonipecotate in 50 mL of DMSO and 66 mL of methanol was stirred, and 44 mL (0.256 mole) of N,N-diisopropylethylamine, followed by 22.8 grams (0.085 mole) of 5-[4-(bromomethyl)phenyl]-2-ethyl-1,2,3,4-tetraazole were added. Upon completion of addition, the reaction mixture was stirred at ambient temperature for about 72 hours. After this time, the reaction mixture was diluted with 130 mL of ethyl acetate, and washed with a 1:1 solution of an aqueous solution saturated with sodium chloride and water. The organic layer was then washed with an aqueous solution saturated with sodium chloride and water, dried with sodium sulfate, and filtered. The filtrate was concentrated under reduced pressure to a residue. The residue was purified with column chromatography on silica gel using mixtures of methylene chloride and acetone. The appropriate fractions were combined and concentrated under reduced pressure, yielding 20.9 grams of the subject compound. The NMR spectrum was consistent with the proposed structure.

Step E Synthesis of 1-{[4-(2-ethyl-1,2,3,4-tetraazol-5-yl)phenyl]methyl}piperidinecarboxylic acid as an Intermediate A solution of 20.9 grams (0.078 mole) of ethyl 1-{[4-(2-ethyl-1,2,3,4-tetraazol-5-yl)phenyl]methyl}piperidine-4-carboxylate in 132 mL of THF was stirred, and a solution of 3.4 grams (0.086 mole) of sodium hydroxide in 93 mL of water, followed by 80 mL of methanol were added. Upon completion of addition, the reaction mixture was stirred at ambient temperature for two hours. After this time, the reaction mixture was concentrated under reduced pressure to a residue. The residue was taken up in toluene and concentrated under reduced pressure to remove any remaining solvents. The residue was dissolved in 100 mL of water and extracted with diethyl ether. The aqueous layer was cooled to about −2° C., and was brought to a pH of 7 with concentrated hydrochloric acid. The resultant solid was collected by filtration, washed with water, and dried, yielding 18.2 grams of the subject compound. The NMR spectrum was consistent with the proposed structure.

Step F Synthesis of 1-{[4-(2-ethyl(1,2,3,4-tetraazol-5-yl))phenyl]methyl}(4-piperidyl)-N-methoxy-N-methylcarboxamide as an Intermediate A solution of 18.2 grams (0.058 mole) of 1-{[4-(2-ethyl-1,2,3,4-tetraazol-5-yl)phenyl]methyl}piperidinecarboxylic acid in 240 mL of DMF was stirred, and 6.8 grams (0.070 mole) of N,O-dimethylhydroxylamine hydrochloride was added. The reaction mixture was cooled to 0° C., and 11.3 grams (0.070 mole) of diethyl cyanophosphonate, followed by 17.8 mL (0.127 mole) of triethylamine were added. Upon completion of addition, the reaction mixture was stirred for two hours, and then it was diluted with ethyl acetate and a 1:1 solution of an aqueous solution saturated with sodium chloride and water. To aid in separating the organic layer from the aqueous layer, hexane and solid sodium chloride were added to the reaction mixture. The organic layer was organic layer was separated and washed with water, and then with an aqueous solution saturated with sodium chloride. The mixture was dried with sodium sulfate, filtered, and concentrated under reduced pressure, yielding 18.5 grams of the subject compound. The NMR spectrum was consistent with the proposed structure.

Step G Synthesis of 1-{[4-(2-ethyl(1,2,3,4-tetraazol-5-yl))phenyl]methyl}(4-piperidyl)4-(trifluoromethoxy)phenyl ketone (Compound 72) as an Intermediate To a Grignard Reagent prepared from 9.3 grams (0.039 mole) of 1-bromo-4-trifluoromethoxybenzene and 1.0 gram (0.041 gram-atom) of magnesium metal in 27 mL of THF was added a solution of 9.3 grams (0.026 mole) of 1-{[4-(2-ethyl(1,2,3,4-tetraazol-5-yl))phenyl]methyl}(4-piperidyl)-N-methoxy-N-methylcarboxamide in 13 mL of THF. Upon completion of addition, the reaction mixture was stirred at ambient temperature for 90 minutes, and then it was warmed to 70° C., where it stirred for an additional 60 minutes. After this time, the reaction mixture was poured into a cold solution of 13 mL of concentrated hydrochloric acid in 93 mL of ethanol, and stirred for ten minutes. The mixture was diluted methylene chloride and washed with an aqueous dilute solution of sodium bicarbonate. The organic layer was dried with sodium sulfate and filtered. The filtrate was concentrated under reduced pressure to a residue, yielding 10.2 grams of the subject compound. The NMR spectrum was consistent with the proposed structure.

Step H Synthesis of Compound 149

A solution of 0.50 gram (0.001 mole) of 1-{[4-(2-ethyl (1,2,3,4-tetraazol-5-yl))phenyl]methyl}(4-piperidyl)4-(trifluoromethoxy)phenyl ketone (Compound 72) in 7.5 mL of ethanol was stirred, and 0.24 gram (0.001 mole) of 4-(trifluoromethoxy)benzoic acid hydrazide was added. Upon completion of addition, the reaction mixture was warmed to 100° C., where it stirred for about 72 hours. After this time, the reaction mixture was cooled to ambient temperature, and a solid was collected by filtration. The filtrate was concentrated under reduced pressure to a residue. The residue was purified with column chromatography on alumina using hexane, methylene chloride, and mixtures thereof as eluants. The appropriate fractions were combined and concentrated under reduced pressure, yielding Compound 149. The NMR spectrum was consistent with the proposed structure.

EXAMPLE 3

This example illustrates one protocol for the preparation of 2-{4-[(4-{bis[4-(trifluoromethyl)phenyl] methyl}piperazinyl)methyl]phenoxy}pyrimidine (Compound 169 in Table Below)

Step A Synthesis of 2-[4-(chloromethyl)phenoxy]pyrimidine as an Intermediate

A stirred solution of 4.0 grams (0.02 mole) of (4-pyrimidin-2-yloxyphenyl)methanol (known compound-CA Registry Number 344333-77-3) and seven drops of pyridine in 35 mL of methylene chloride was cooled in an ice-water bath and a solution of 2.0 mL (0.027 mole) of thionyl chloride was added dropwise. Upon completion of addition the reaction mixture was stirred at about 10° C. to 20° C. during a three-hour period. After this time, the reaction mixture was poured into a cold aqueous solution of sodium bicarbonate. The mixture was then stirred for 30 minutes and the organic layer was separated. The aqueous layer was extracted with one 50 mL portion of methylene chloride. The extract was combined with the organic layer, and the combination was passed through silicone-coated filter paper to remove traces of water. The filtrate was concentrated under reduced pressure, yielding grams of the subject compound. The NMR spectrum was consistent with the proposed structure.

Step B Synthesis of Compound 169

A mixture of 0.39 gram (0.001 mole) of {bis[4-(trifluoromethyl)phenyl]methyl}piperazine (known compound—as prepared in PCT Publication WO 97/26252), 0.22 gram (0.001 mole) of 2-[4-(chloromethyl)phenoxy]pyrimidine and 0.5 mL of diisopropylethylamine in 1 mL of DMSO was sealed in a vial and stirred at ambient temperature for an 18 hour period. After this time, the reaction mixture was poured into an aqueous solution saturated with sodium chloride. The resultant mixture was extracted with ethyl acetate, and the extract was dried with magnesium sulfate. The mixture was filtered, and the filtrate concentrated under reduced pressure, yielding 0.5 gram of Compound 169. The NMR spectrum was consistent with the proposed structure.

EXAMPLE 4

This Example Illustrates One Protocol for the Preparation of 2-{4-[(4-{bis[4-(trifluoromethyl)phenyl]methyl}1-oxypiperazinyl)methyl]phenoxy}pyrimidine (Compound 180 in Table Below)

A solution of 0.35 gram (0.0006 mole) of Compound 169, prepared in Example 13 above) and 1 mL of 50% hydrogen peroxide in 10 mL of methanol was stirred at ambient temperature for an 18 hour period. Analysis of the reaction mixture using liquid chromatography-mass spectroscopy (LC-MS) after this time indicated that the reaction had not gone to completion. An additional 1 mL of 50% hydrogen peroxide was added and the reaction mixture was stirred at ambient temperature during a 60 hour period. The reaction mixture was again analyzed with LC-MS and was determined to be complete. The reaction mixture was concentrated under reduced pressure to a residue. The residue was dissolved in ethyl acetate and dried with magnesium sulfate. The mixture was filtered and the filtrate was concentrated under reduced pressure, yielding 0.33 gram of Compound 180. The NMR spectrum was consistent with the proposed structure.

EXAMPLE 5

This Example Illustrates One Protocol for the Preparation of {4-[2-(1-{[2-ethyl(1,2,3,4-tetrazol-5-yl))phenyl]methyl}(4-piperidyl))(1,3-dioxolan-2-yl)]phenoxy}trifluoromethane (Compound 85 in Table Below)

In a reaction vessel equipped with a Dean-Stark trap, a solution of 1-{[4-(2-ethyl(1,2,3,4-tetraazol-5-yl))phenyl]methyl}(4-piperidyl)4-(trifluoromethoxy)phenyl ketone (Compound 72-prepared in Example 2), a slight excess of ethylene glycol and a catalytic amount of p-toluenesulfonic acid in toluene is heated at reflux until the theoretical amount of water is collected. The reaction mixture is concentrated under reduced pressure to a residue, which is purified with column chromatography, providing Compound 82.

EXAMPLE 6

This Example Illustrates One Protocol for the Preparation of 2-[4-({4-[1,2-bis(4-chlorophenyl)ethyl]-1-oxypiperazinyl}methyl)phenoxy]pyridine (Compound 182 in Table Below)

Step A Synthesis of ethyl 4-[(4-(2-pyridyloxy)phenyl)methyl]piperazinecarboxylate as an Intermediate This compound was prepared in a manner analogous to that of Example 2, Step D, using 2.2 grams (0.010 mole) of 4-(2-pyridyloxy)phenylmethyl chloride, 1.6 grams (0.010 mole) of ethyl 1-piperazinecarboxylate, and 3.9 grams (0.030 mole) of DMSO, yielding 3.4 grams of the subject compound. The NMR spectrum was consistent with the proposed structure.

Step B Synthesis of ethyl 4-[(4-(2-pyridyloxy)phenyl)methyl]-4-oxypiperazinecarboxylate as an Intermediate A solution of 1.0 gram (0.0029 mole) of ethyl 4-[(4-(2-pyridyloxy)phenyl)methyl]piperazinecarboxylate and 1.6 grams (excess) of 30% hydrogen peroxide in 30 mL of methanol was stirred at ambient temperature during an 18 hour period. After this time the reaction mixture was concentrated under reduced pressure to a residue. The residue was dissolved in ethyl acetate and washed with water. The organic layer was concentrated under reduced pressure, yielding about 1.0 gram of the subject compound. The NMR spectrum was consistent with the proposed structure.

Step C Synthesis of 2-[4-(4-oxypiperazin-1-ylmethyl)phenoxy]pyridine as an Intermediate A stirred solution of 1.0 gram (0.003 mole) of ethyl 4-[(4-(2-pyridyloxy)phenyl)methyl]4-oxypiperazinecarboxylate and 15 mL of 50% aqueous sodium hydroxide in 15 mL of 1:1 THF:methanol was heated to 80° C. where it was maintained for an 18 hour period. After this time, the reaction mixture was concentrated under reduced pressure to a residue, and the residue was washed with two portions of acetonitrile. The combined extracts were dried with magnesium sulfate and filtered. The filtrate was concentrated under reduced pressure, yielding 0.6 gram of the sunject compound.

Step D Synthesis of 1,2-di(4-chlorophenyl)ethan-1-ol as an Intermediate

A solution of 1,2-di(4-chlorophenyl)ethan-1-one (known compound) and sodium borohydride in methanol is stirred at ambient temperature for about three hours. After this time, the reaction mixture is cooled, and water is carefully added to destroy excess sodium borohydride. The mixture is cooled to 0° C. and neutralized with concentrated hydrochloric acid. The mixture is concentrated under reduced pressure to remove some of the methanol. The concentrate is taken up in ethyl acetate and washed with an aqueous solution saturated with sodium chloride. The organic layer is dried with sodium sulfate, filtered, and concentrated under reduced pressure, yielding the subject compound.

Step E Synthesis of 4-chloro-1-[2-chloro-2-(4-chlorophenyl)ethyl]benzene as an Intermediate A stirred solution of of thionyl chloride in toluene is cooled to 0° C., and a catalytic amount of pyridine is added. A solution of 1,2-di(4-chlorophenyl)ethan-1-ol in toluene is then added drop wise. Upon completion addition of addition, the reaction mixture is allowed to warm to ambient temperature where it stirs for about 30 minutes. The reaction mixture is washed with water, dried with sodium sulfate, filtered, and concentrated under reduced pressure, yielding the subject compound.

Step F Synthesis of Compound 182

A solution of 4-chloro-1-[2-chloro-2-(4-chlorophenyl)ethyl]benzene and 2-[4-(4-oxypiperazin-1-ylmethyl)phenoxy]pyridine (prepared as in Step C of this Example) in DMSO is stirred, and diisopropylethylamine is added. Upon completion of addition, the reaction mixture is stirred until reaction is complete. The reaction mixture is then diluted with water and extracted with ethyl acetate. The extract is dried with magnesium sulfate, filtered, and concentrated under reduced pressure to a residue. The residue is purified with column chromatography, yielding Compound 182.

The following table sets forth some additional examples of compounds of formula I useful in the present invention:

TABLE 1

Insecticidal N-substituted-4-(substituted arylmethyl)piperidines and Piperazines

I

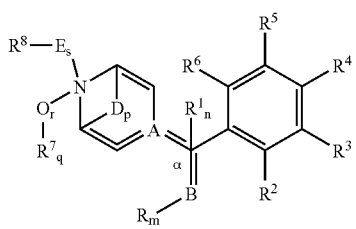

Compounds of formula I where A is CH, forming a piperidine ring; p, q, and r are 0; m and n are 0, where B is O forming a carbonyl group with the methyl carbon (α); and $R^2$, $R^3$, $R^5$, and $R^6$ are hydrogen:

I

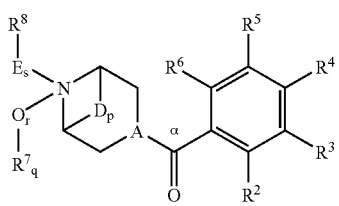

| Cmpd No. | $R^4$ | s | E | x | $R^{27}/R^{28}$ | y | $R^{29}/R^{30}$ | $R^8$ |
|---|---|---|---|---|---|---|---|---|
| 1[1] | H | 0 | — | — | — | — | — | H |
| 2[1] | Cl | 0 | — | — | — | — | — | H |
| 3 | $CF_3$ | 0 | — | — | — | — | — | H |
| 4[1] | $OCH_3$ | 0 | — | — | — | — | — | H |
| 5 | $OCF_3$ | 0 | — | — | — | — | — | H |
| 6[2] | $OCF_3$ | 0 | — | — | — | — | — | H |
| 7 | H | 0 | — | — | — | — | — | $CH_3$ |
| 8[1] | H | 0 | — | — | — | — | — | $CH_3$ |
| 9 | $OCF_3$ | 0 | — | — | — | — | — | $C_2H_5$ |
| 10 | $OCF_3$ | 0 | — | — | — | — | — | $C_4H_9$ |
| 11 | $OCF_3$ | 0 | — | — | — | — | — | cyclopropylmethyl |
| 12 | $OCF_3$ | 0 | — | — | — | — | — | cyclohexylmethyl |
| 13 | $OCF_3$ | 0 | — | — | — | — | — | $C_2H_4OC_2H_5$ |
| 14 | F | 0 | — | — | — | — | — | 5-nitropyrid-2-yl |
| 15 | $OCF_3$ | 0 | — | — | — | — | — | 6-methoxy-1,2,3,4-tetrahydronaphthylen-1-yl |
| 16 | F | 1 | $(CR^{27}R^{28})_x$—$(CR^{29}R^{30})_y$ | 1 | H/H | 0 | — | 3-(4-$CH_3OPh$)pyrazol-4-yl |
| 17 | $OCF_3$ | 1 | $(CR^{27}R^{28})_x$—$(CR^{29}R^{30})_y$ | 1 | H/H | 0 | — | benzo[b]thiophen-2-yl |
| 18 | F | 1 | $(CR^{27}R^{28})_x$—$(CR^{29}R^{30})_y$ | 1 | H/H | 1 | H/H | 5-hydropyridino[1,2a]pyrimidin-4-on-2-yl |
| 19[3] | F | 1 | $(CR^{27}R^{28})_x$—$(CR^{29}R^{30})_y$ | 1 | H/H | 1 | H/H | 1,3-dihydroquinazolin-2,4-dion-3-yl |
| 20[4] | F | 1 | $(CR^{27}R^{28})_x$—$(CR^{29}R^{30})_y$ | 1 | H/H | 1 | H/H | 1,3-dihydroquinazolin-2,4-dion-3-yl |

TABLE 1-continued

Insecticidal N-substituted-4-(substituted arylmethyl)piperidines and Piperazines Compounds of formula I where A is CH, forming a piperidine ring; p, q, and r are 0, s is 1, and m and n are 0; where B is O forming a carbonyl group with the methyl carbon (α); $R^3$, $R^5$, and $R^6$ are hydrogen; E is, unless otherwise noted, —$(CR^{27}R^{28})_x$—$(CR^{29}R^{30})_y$, where x is 1 and y is 0; and $R^8$ is phenyl substituted with $R^{22}$, $R^{23}$, $R^{24}$, $R^{25}$, and $R^{26}$; where $R^{25}$, $R^{26}$, $R^{27}$ and $R^{28}$ are hydrogen:

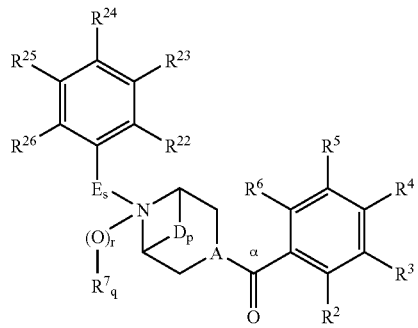

I

| Cmpd. No | $R^2$ | $R^4$ | $R^{22}/R^{23}$ | $R^{24}$ |
|---|---|---|---|---|
| 21 | H | H | H/H | H |
| 22 | H | H | H/H | H |
| 23 | H | H | H/H | F |
| 24 | H | F | H/H | H |
| 25 | H | $OCF_3$ | H/H | H |
| 26 | H | $OCF_3$ | H/H | Br |
| 27 | H | $OCF_3$ | H/H | F |
| 28 | H | H | H/H | F |
| 29 | H | $CF_3$ | H/H | C≡N |
| 30 | H | $OCF_3$ | H/H | $CH_3$ |
| 31 | H | $OCF_3$ | $OCH_3$/H | H |
| 32 | H | $OCF_3$ | H/$OCH_3$ | H |
| 33 | H | $OC_3H_7$ | H/H | OH |
| 34 | H | H | H/H | $OCH_3$ |
| 35 | H | $OCF_3$ | H/H | $OCH_3$ |
| 36[1] | H | $OCF_3$ | H/H | $OCH_3$ |
| 37 | H | $OCF_3$ | H/H | $SCH_3$ |
| 38 | H | H | H/H | $OC_3H_7$ |
| 39 | $C_2H_5$ | H | H/H | $OC_3H_7$ |
| 40 | H | $CF_3$ | H/H | $OC_3H_7$ |
| 41[1] | H | $CF_3$ | H/H | $OC_3H_7$ |
| 42 | H | $C_3F_7$ | H/H | $OC_3H_7$ |
| 43 | H | $OCF_3$ | H/H | $OC_3H_7$ |
| 44 | H | $SCH_3$ | H/H | $OC_3H_7$ |
| 45 | H | $OCF_3$ | $SCH_3$/H | $OC_3H_7$ |
| 46 | $CF_3$ | $CF_3$ | H/H | $OC_3H_7$ |
| 47 | H | $OCF_3$ | H/H | $OCH(CH_3)_2$ |
| 48 | H | $OCF_3$ | H/H | $OCH_2CH(CH_3)_2$ |
| 49 | H | $OCF_3$ | H/H | $OC_2H_4CH(CH_3)_2$ |
| 50 | H | $OCF_3$ | H/H | $OCH_2OCH_3$ |
| 51 | H | $OCF_3$ | H/H | $OC_3H_6CH=CH_2$ |
| 52 | H | $OCF_3$ | H/H | $OCH_2CH=CHCl$ |
| 53 | H | H | H/H | $OCH_2C(Cl)=CH_2$ |
| 54 | H | $OCF_3$ | H/H | $OCH_2C(Cl)=CH_2$ |
| 55 | H | $OCF_3$ | H/H | $OCH_2CH=C(CH_3)_2$ |
| 56 | H | $OCF_3$ | H/H | CHO |
| 57 | H | $OCF_3$ | H/H | $CO_2CH(CH_3)_2$ |
| 58 | H | $OCF_3$ | H/H | $SO_2C_3H_7$ |
| 59 | H | $OCF_3$ | H/H | $NHCO_2CH_3$ |
| 60 | H | $OCF_3$ | H/H | $CH=NOC_2H_5$ |
| 61 | H | $OCF_3$ | H/H | 4-$FPhCH_2O$ |
| 62 | H | $OCF_3$ | H/H | pyrid-2-yl |
| 63 | H | $OCF_3$ | H/H | pyrid-2-yloxy |
| 64 | H | $CF_3$ | H/H | 5-chloropyrid-2-yloxy |
| 65 | H | Cl | H/H | 2-methyl-2H-tetrazol-5-yl |
| 66 | H | $CF_3$ | H/H | 2-methyl-2H-tetrazol-5-yl |
| 67 | H | $OCF_3$ | H/H | 2-methyl-2H-tetrazol-5-yl |
| 68 | H | H | H/H | 2-ethyl-2H-tetrazol-5-yl |
| 69 | H | Cl | H/H | 2-ethyl-2H-tetrazol-5-yl |
| 70 | H | F | H/H | 2-ethyl-2H-tetrazol-5-yl |
| 71 | H | $CF_3$ | H/H | 2-ethyl-2H-tetrazol-5-yl |

TABLE 1-continued

Insecticidal N-substituted-4-(substituted arylmethyl)piperidines and Piperazines

| | | | | |
|---|---|---|---|---|
| 72 | H | OCF$_3$ | H/H | 2-ethyl-2H-tetrazol-5-yl |
| 73 | H | OCF$_3$ | H/H | 2-(2-fluoroethyl)-2H-tetrazol-5-yl |
| 74 | H | OCF$_3$ | H/H | CH$_3$ |
| 75* | H | CF$_3$ | H/H | OCF$_3$ |
| 76* | H | H | H/H | 4-chloronaphth-1-yloxymethyl |

*In Cmpds 75 and 76, E is —(CR$^{27}$R$^{28}$)$_x$—(CR$^{29}$R$^{30}$)$_y$O—, where x and y are 1 and R$^{27}$–R$^{30}$ are hydrogen.

Compounds of formula I where A is CH, forming a piperidine ring; p is 0; q is 0 and r is 1, forming an N-oxide; s is 1; n and m are 0; where B is O forming a carbonyl group with the methyl carbon (α); E is —(CR$^{27}$R$^{28}$)$_x$—(CR$^{29}$R$^{30}$)$_y$—, where x is 1, and y is 0; and R$^8$ is phenyl substituted with R$^{22}$, R$^{23}$, R$^{24}$, R$^{25}$, and R$^{26}$; where R$^2$, R$^3$, R$^5$, R$^6$, R$^{22}$, R$^{23}$, R$^{25}$, R$^{26}$, R$^{27}$ and R$^{28}$ are hydrogen:

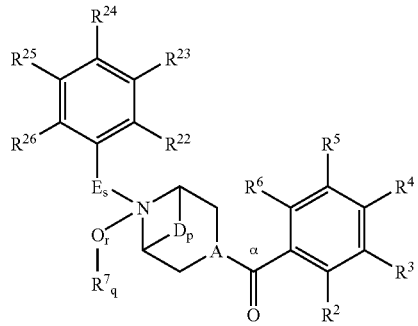

I

| Cmpd. No | R$^4$ | R$^{24}$ |
|---|---|---|
| 77 | CF$_3$ | OC$_3$H$_7$ |
| 78 | CF$_3$ | 2-ethyl-2H-tetrazol-5-yl |

Compounds of formula I where A is CH, forming a piperidine ring; p, q, r and m are 0; n and s are 1; where B and R$^1$ are taken together with —G—CH(R$^{14}$)—(CH$_2$)$_y$—J—, and with the methyl carbon (α), form a heterocyclic derivative; E is —(CR$^{27}$R$^{28}$)$_x$—(CR$^{29}$R$^{30}$)$_y$—, where x is 1, and y is 0; and R$^8$ is phenyl substituted with R$^{22}$, R$^{23}$, R$^{24}$, R$^{25}$, and R$^{26}$; where R$^2$, R$^3$, R$^5$, R$^6$, R$^{22}$, R$^{23}$, R$^{25}$, R$^{26}$, R$^{27}$ and R$^{28}$ are hydrogen:

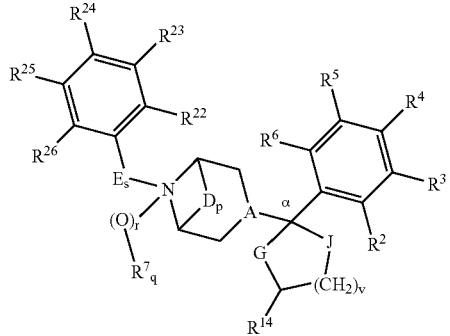

I

| Cmpd. No. | G | J | v | R$^4$ | R$^{14}$ | R$^{24}$ |
|---|---|---|---|---|---|---|
| 79 | O | O | 1 | CF$_3$ | H | H |
| 80 | O | S | 1 | CF$_3$ | H | H |
| 81 | S | S | 1 | CF$_3$ | H | H |

TABLE 1-continued

Insecticidal N-substituted-4-(substituted arylmethyl)piperidines and Piperazines

| 82 | O | O | 2 | $CF_3$ | H | H |
| 83 | O | O | 1 | $OCF_3$ | H | H |
| 84 | O | O | 1 | $CF_3$ | H | 2-ethyl-2H-tetrazol-5-yl |
| 85 | O | O | 1 | $OCF_3$ | H | 2-ethyl-2H-tetrazol-5-yl |
| 86 | O | O | 1 | $OCF_3$ | H | pyrid-2-yloxy |
| 87 | O | O | 1 | $CF_3$ | 4-chlorophenyl | H |
| 88 | O | O | 1 | $CF_3$ | 4-trifluoromethylphenyl | H |
| 89 | S | S | 1 | $CF_3$ | 4-chlorophenyl | H |

Compounds of formula I, where A is CH, forming a piperidine ring; n is 0, forming a double bond from the methyl carbon (α) to B, where B is a bridging group from the methyl carbon to R; p, q, and r are 0; m and s are 1; E is —$(CR^{27}R^{28})_x$—$(CR^{291}R^{30})_y$—, where x is 1, and y is 0; $R^8$ is phenyl substituted with $R^{22}$, $R^{23}$, $R^{24}$, $R^{25}$, and $R^{26}$; where $R^2$, $R^3$, $R^5$, $R^6$, $R^{22}$, $R^{23}$, $R^{25}$, $R^{26}$, $R^{27}$ and $R^{28}$ are hydrogen:

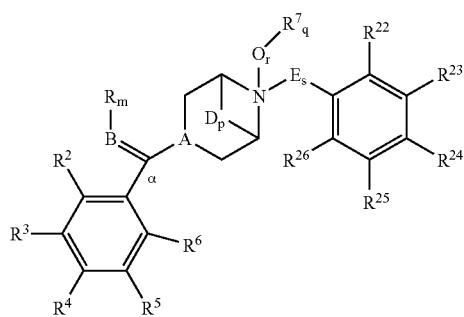

I

| Cmpd. No. | R | $R^4$ | B | $R^{15}$ | $R^{24}$ |
|---|---|---|---|---|---|
| 90 | $C(CH_3)_2$ | $OCF_3$ | NN= | — | 2-ethyl-2H-tetrazol-5-yl |
| 91 | $CH(CH_3)_2$ | $CF_3$ | $NNR^{15}$ | H | 2-methyl-2H-tetrazol-5-yl |
| 92 | pyrid-2-yl | $OCF_3$ | $NNR^{15}$ | H | 2-ethyl-2H-tetrazol-5-yl |

Compounds of formula I, where A is CH, forming a piperidine ring; n is 0, forming a double bond from the methyl carbon (α) to B, where B is a bridging group from the methyl carbon to R; p, q, and r are 0; m and s are 1; R is phenyl substituted with $R^{17}$, $R^{18}$ $R^{19}$, $R^{20}$, and $R^{21}$; where $R^2$, $R^3$, $R^5$, $R^6$, $R^{17}$, $R^{18}$, $R^{20}$ and $R^{21}$ are hydrogen:

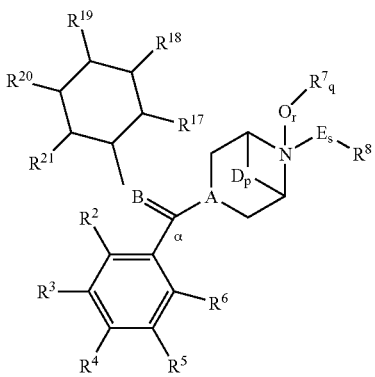

I

| Cmpd. No. | $R^4$ | E | $R^8$ | B | $R^{15}$ | $R^{16}$ | $R^{19}$ |
|---|---|---|---|---|---|---|---|
| 93 | $OCF_3$ | C(=O) | $OCH_3$ | $NNR^{15}C(=O)NR^{16}$ | H | H | $OCF_3$ |

TABLE 1-continued

Insecticidal N-substituted-4-(substituted arylmethyl)piperidines and Piperazines Compounds of formula I, where A is CH, forming a piperidine ring; n is 0, forming a double bond
from the methyl carbon (α) to B, where B is a bridging group from the methyl carbon to R;
p, q, and r are 0; m and s are 1; E is —$(CR^{27}R^{28})_x$—$(CR^{29}R^{30})_y$—,
where x is 1, and y is 0; $R^8$ is phenyl substituted with
$R^{22}$, $R^{23}$, $R^{24}$, $R^{25}$, and $R^{26}$; and R is phenyl substituted with $R^{17}$, $R^{18}$ $R^{19}$,
$R^{20}$, and $R^{21}$; where $R^2$, $R^3$, $R^5$, $R^6$, $R^9$, $R^{21}$, $R^{22}$, $R^{23}$, $R^{25}$, $R^{26}$, $R^{27}$, and $R^{28}$ are hydrogen:

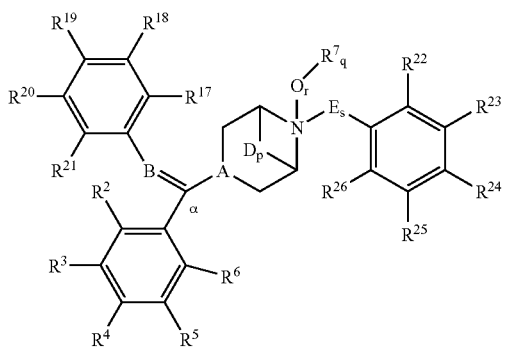

I

| Cmpd. No. | $R^4$ | $R^{24}$ | $R^{17}$ | $R^{18}$ | $R^{19}$ | $R^{20}$ | B | $R^{15}/R^{16}$ |
|---|---|---|---|---|---|---|---|---|
| 94 | Cl | 2-ethyl-2H-tetrazol-5-yl | H | H | OCF$_3$ | H | CH | — |
| 95 | OCF$_3$ | cyclohexyl | H | H | OCF$_3$ | H | NNR$^{15}$ | H |
| 96 | OCF$_3$ | OCH$_3$ | H | H | OCF$_3$ | H | NNR$^{15}$ | H |
| 97 | OCF$_3$ | OC$_3$H$_7$ | H | H | OCF$_3$ | H | NNR$^{15}$ | H |
| 98 | OCF$_3$ | OCH(CH$_3$)$_2$ | H | H | OCF$_3$ | H | NNR$^{15}$ | H |
| 99 | OCF$_3$ | OCH$_2$CH(CH$_3$)$_2$ | H | H | OCF$_3$ | H | NNR$^{15}$ | H |
| 100 | OCF$_3$ | CO$_2$CH(CH$_3$)$_2$ | H | H | OCF$_3$ | H | NNR$^{15}$ | H |
| 101 | CF$_3$ | 5-chloropyrid-2-yloxy | H | H | OCF$_3$ | H | NNR$^{15}$ | H |
| 102 | OCF$_3$ | 2-ethyl-2H-tetrazol-5-yl | H | H | H | H | NNR$^{15}$ | H |
| 103 | CF$_3$ | 2-ethyl-2H-tetrazol-5-yl | Cl | H | H | H | NNR$^{15}$ | H |
| 104 | OCF$_3$ | 2-ethyl-2H-tetrazol-5-yl | Cl | H | H | H | NNR$^{15}$ | H |
| 105 | OCF$_3$ | 2-ethyl-2H-tetrazol-5-yl | H | Cl | H | H | NNR$^{15}$ | H |
| 106 | CF$_3$ | 2-ethyl-2H-tetrazol-5-yl | H | H | Cl | H | NNR$^{15}$ | H |
| 107 | CF$_3$ | 2-ethyl-2H-tetrazol-5-yl | H | H | Br | H | NNR$^{15}$ | H |
| 108 | CF$_3$ | 2-ethyl-2H-tetrazol-5-yl | H | H | I | H | NNR$^{15}$ | H |
| 109 | OCF$_3$ | 2-ethyl-2H-tetrazol-5-yl | H | H | I | H | NNR$^{15}$ | H |
| 110 | OCF$_3$ | 2-ethyl-2H-tetrazol-5-yl | Cl | H | H | Cl | NNR$^{15}$ | H |
| 111 | OCF$_3$ | 2-ethyl-2H-tetrazol-5-yl | H | Cl | Cl | H | NNR$^{15}$ | H |
| 112 | OCF$_3$ | 2-ethyl-2H-tetrazol-5-yl | H | Cl | H | Cl | NNR$^{15}$ | H |
| 113 | OCF$_3$ | 2-ethyl-2H-tetrazol-5-yl | H | H | CH$_3$ | H | NNR$^{15}$ | H |
| 114 | OCF$_3$ | 2-ethyl-2H-tetrazol-5-yl | H | H | CH(CH$_3$)$_2$ | H | NNR$^{15}$ | H |
| 115 | CF$_3$ | 2-ethyl-2H-tetrazol-5-yl | H | H | C(CH$_3$)$_3$ | H | NNR$^{15}$ | H |
| 116 | OCF$_3$ | 2-ethyl-2H-tetrazol-5-yl | H | H | OCH$_3$ | H | NNR$^{15}$ | H |
| 117 | CF$_3$ | 2-methyl-2H-tetrazol-5-yl | H | H | CF$_3$ | H | NNR$^{15}$ | H |

TABLE 1-continued

Insecticidal N-substituted-4-(substituted arylmethyl)piperidines and Piperazines

| | | | | | | | | |
|---|---|---|---|---|---|---|---|---|
| 118 | $CF_3$ | 2-ethyl-2H-tetrazol-5-yl | H | H | $CF_3$ | H | $NNR^{15}$ | H |
| 119 | $CF_3$ | 2-ethyl-2H-tetrazol-5-yl | H | H | $OCF_3$ | H | $NNR^{15}$ | H |
| 120 | $OCF_3$ | 2-ethyl-2H-tetrazol-5-yl | $CF_3$ | H | H | H | $NNR^{15}$ | H |
| 121 | $OCF_3$ | 2-ethyl-2H-tetrazol-5-yl | H | $CF_3$ | H | H | $NNR^{15}$ | H |
| 122 | $OCF_3$ | 2-ethyl-2H-tetrazol-5-yl | H | H | $CF_3$ | H | $NNR^{15}$ | H |
| 123 | $OCF_3$ | 2-methyl-2H-tetrazol-5-yl | H | H | $OCF_3$ | H | $NNR^{15}$ | H |
| 124 | $OCF_3$ | 2-ethyl-2H-tetrazol-5-yl | H | H | $OCF_3$ | H | $NNR^{15}$ | H |
| 125 | $OCF_3$ | 2-ethyl-2H-tetrazol-5-yl | H | H | $SO_2NH_2$ | H | $NNR^{15}$ | H |
| 126 | $OCF_3$ | 2-ethyl-2H-tetrazol-5-yl | H | H | $NO_2$ | H | $NNR^{15}$ | H |
| 127 | $OCF_3$ | 2-ethyl-2H-tetrazol-5-yl | H | H | $CF_3$ | H | $NNR^{15}CH_2$ | H |
| 128 | $OCF_3$ | 2-ethyl-2H-tetrazol-5-yl | H | H | $OCF_3$ | H | $NNR^{15}CH_2$ | H |
| 129 | $OCF_3$ | 2-ethyl-2H-tetrazol-5-yl | H | H | $CF_3$ | H | $NNR^{15}SO_2$ | H |
| 130 | $OCF_3$ | 2-ethyl-2H-tetrazol-5-yl | H | H | $OCF_3$ | H | $NNR^{15}SO_2$ | H |
| 131 | $OCF_3$ | pyrid-2-yloxy | H | H | Cl | H | $NNR^{15}C(=O)$ | H |
| 132 | $OCF_3$ | pyrid-2-yloxy | H | H | $CF_3$ | H | $NNR^{15}C(=O)$ | H |
| 133 | $OCF_3$ | pyrid-2-yloxy | H | H | $OCF_3$ | H | $NNR^{15}C(=O)$ | H |
| 134 | $OCF_3$ | pyrid-2-yloxy | H | H | $CF_3$ | H | $NNR^{15}C(=O)$ | 4-$CF_3$PhC(=O) |
| 135 | $OCF_3$ | 2-methyl-2H-tetrazol-5-yl | H | H | H | H | $NNR^{15}C(=O)$ | H |
| 136 | $OCF_3$ | 2-methyl-2H-tetrazol-5-yl | Cl | H | H | H | $NNR^{15}C(=O)$ | H |
| 137 | $OCF_3$ | 2-methyl-2H-tetrazol-5-yl | H | Cl | H | H | $NNR^{15}C(=O)$ | H |
| 138 | Cl | 2-methyl-2H-tetrazol-5-yl | H | H | Cl | H | $NNR^{15}C(=O)$ | H |
| 139 | $OCF_3$ | 2-methyl-2H-tetrazol-5-yl | H | H | Cl | H | $NNR^{15}C(=O)$ | H |
| 140 | $OCF_3$ | 2-methyl-2H-tetrazol-5-yl | H | H | Br | H | $NNR^{15}C(=O)$ | H |
| 141 | $OCF_3$ | 2-methyl-2H-tetrazol-5-yl | F | H | H | H | $NNR^{15}C(=O)$ | H |
| 142 | $OCF_3$ | 2-methyl-2H-tetrazol-5-yl | H | F | H | H | $NNR^{15}C(=O)$ | H |
| 143 | $OCF_3$ | 2-methyl-2H-tetrazol-5-yl | H | H | F | H | $NNR^{15}C(=O)$ | H |
| 144 | $OCF_3$ | 2-methyl-2H-tetrazol-5-yl | H | H | I | H | $NNR^{15}C(=O)$ | H |
| 145 | $OCF_3$ | 2-methyl-2H-tetrazol-5-yl | H | H | $CH_3$ | H | $NNR^{15}C(=O)$ | H |
| 146 | $OCF_3$ | 2-methyl-2H-tetrazol-5-yl | H | H | $OCH_3$ | H | $NNR^{15}C(=O)$ | H |
| 147 | $OCF_3$ | 2-ethyl-2H-tetrazol-5-yl | H | H | $CF_3$ | H | $NNR^{15}C(=O)$ | H |
| 148 | $OCF_3$ | 2-methyl-2H-tetrazol-5-yl | H | H | $OCF_3$ | H | $NNR^{15}C(=O)$ | H |
| 149 | $OCF_3$ | 2-ethyl-2H-tetrazol-5-yl | H | H | $OCF_3$ | H | $NNR^{15}C(=O)$ | H |
| 150 | $OCF_3$ | 2-ethyl-2H-tetrazol-5-yl | H | H | $NO_2$ | H | $NNR^{15}C(=O)$ | H |
| 151 | $OCF_3$ | 2-methyl-2H-tetrazol-5-yl | H | H | $OCF_3$ | H | $NNR^{15}C(=O)$ | $CH_3$ |
| 152 | $OCF_3$ | 2-methyl-2H-tetrazol-5-yl | H | H | $OCF_3$ | H | $NNR^{15}C(=O)$ | $C_2H_5$ |
| 153 | $OCF_3$ | 2-methyl-2H-tetrazol-5-yl | H | H | Cl | H | $NNR^{15}C(=O)$ | $CH(CH_3)_2$ |
| 154 | $CF_3$ | 2-methyl-2H-tetrazol-5-yl | H | H | $CF_3$ | H | $NNR^{15}C(=O)$ | $CH(CH_3)_2$ |
| 155 | $OCF_3$ | 2-methyl-2H-tetrazol-5-yl | H | H | H | H | $NNR^{15}C(=O)$ | PhC(=O) |

TABLE 1-continued

Insecticidal N-substituted-4-(substituted arylmethyl)piperidines and Piperazines

| 156 | OCF$_3$ | 2-methyl-2H-tetrazol-5-yl | Cl | H | H | H | NNR$^{15}$C(=O) | 2-ClPhC(=O) |
| 157 | OCF$_3$ | 2-methyl-2H-tetrazol-5-yl | H | Cl | H | H | NNR$^{15}$C(=O) | 3-ClPhC(=O) |
| 158 | OCF$_3$ | 2-methyl-2H-tetrazol-5-yl | H | H | Cl | H | NNR$^{15}$C(=O) | 4-ClPhC(=O) |
| 159 | OCF$_3$ | 2-methyl-2H-tetrazol-5-yl | H | H | Br | H | NNR$^{15}$C(=O) | 4-BrPhC(=O) |
| 160 | OCF$_3$ | 2-methyl-2H-tetrazol-5-yl | F | H | H | H | NNR$^{15}$C(=O) | 2-FPhC(=O) |
| 161 | OCF$_3$ | 2-methyl-2H-tetrazol-5-yl | H | H | CH$_3$ | H | NNR$^{15}$C(=O) | 4-CH$_3$PhC(=O) |
| 162 | OCF$_3$ | 2-methyl-2H-tetrazol-5-yl | H | H | OCH$_3$ | H | NNR$^{15}$C(=O) | 4-CH$_3$OPhC(=O) |
| 163 | OCF$_3$ | 2-methyl-2H-tetrazol-5-yl | H | H | NO$_2$ | H | NNR$^{15}$C(=O) | 4-NO$_2$PhC(=O) |
| 164 | OCF$_3$ | 2-methyl-2H-tetrazol-5-yl | H | H | CF$_3$ | H | NNR$^{15}$C(=O)NR$^{16}$ | H |
| 165 | OCF$_3$ | 2-ethyl-2H-tetrazol-5-yl | H | H | OCF$_3$ | H | NNR$^{15}$C(=O)NR$^{16}$ | H |
| 166 | OCF$_3$ | 2-ethyl-2H-tetrazol-5-yl | H | H | CF$_3$ | H | NNR$^{15}$C(=S)NR$^{16}$ | H |

Compounds of formula I where A is N, forming a piperazine ring; n is 1, forming single bonds from the methyl carbon (α) and its substituents; p, q, r, and m are 0, s is 1;

E is —(CR$^{27}$R$^{28}$)$_x$—(CR$^{29}$R$^{30}$)$_y$—, where x is 1, and y is 0;

B is phenyl substituted with R$^9$, R$^{10}$, R$^{11}$, R$^{12}$, and R$^{13}$; and R$^8$ is phenyl substituted with R$^{22}$, R$^{23}$, R$^{24}$, R$^{25}$, and R$^{26}$; where R$^1$, R$^2$, R$^3$, R$^5$, R$^6$, R$^9$, R$^{10}$, R$^{12}$, R$^{13}$, R$^{22}$, R$^{23}$, R$^{25}$, R$^{26}$, R$^{27}$, and R$^{28}$ are hydrogen;

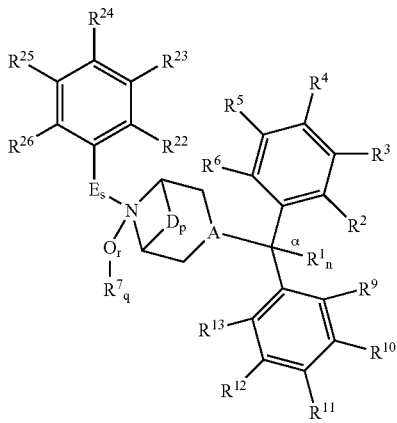

I

| Cmpd. No. | R$^4$ | R$^{11}$ | R$^{24}$ |
|---|---|---|---|
| 167 | Cl | Cl | pyrimidin-2-yloxy |
| 168 | Cl | CF$_3$ | pyrimidin-2-yloxy |
| 169 | CF$_3$ | CF$_3$ | pyrimidin-2-yloxy |
| 170 | OCF$_3$ | OCF$_3$ | 6-chloropyridazin-3-yloxy |

TABLE 1-continued

Insecticidal N-substituted-4-(substituted arylmethyl)piperidines and Piperazines Compounds of formula I where A is N, forming a piperazine ring; n is 1, forming single bonds from the methyl carbon (α) and its substituents; p and m are 0, s is 1; q is 0 and r is 1, forming an N-oxide; E is $-(CR^{27}R^{28})_x-(CR^{29}R^{30})_y-$, where x is 1, and y is 0; B is phenyl substituted with $R^9$, $R^{10}$, $R^{11}$, $R^{12}$, and $R^{13}$; and $R^8$ is phenyl substituted with $R^{22}$, $R^{23}$, $R^{24}$, $R^{25}$, and $R^{26}$; where $R^1$, $R^2$, $R^3$, $R^5$, $R^6$, $R^9$, $R^{10}$, $R^{12}$, $R^{13}$, $R^{22}$, $R^{23}$, $R^{25}$, $R^{26}$, $R^{27}$, and $R^{28}$ are hydrogen;

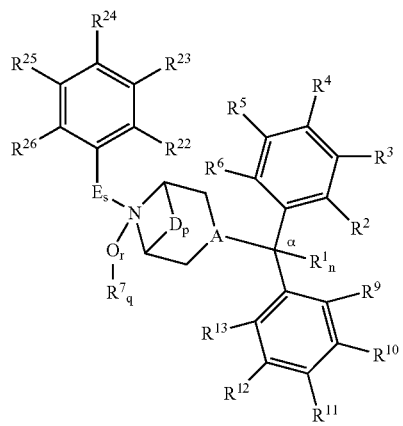

I

| Cmpd. No. | $R^4$ | $R^{11}$ | $R^{24}$ |
|---|---|---|---|
| 171* | $OCF_3$ | $OCF_3$ | $OCH_3$ |
| 172 | $OCF_3$ | $OCF_3$ | O(2-F—Ph) |
| 173 | Cl | $CF_3$ | $NHCO_2CH(CH_3)_2$ |
| 174 | $CF_3$ | $CF_3$ | $NHCO_2CH(CH_3)_2$ |
| 175 | $CF_3$ | $CF_3$ | 2-ethyl-2H-tetrazol-5-yl |
| 176 | Cl | $CF_3$ | pyrid-2-yloxy |
| 177 | $CF_3$ | $CF_3$ | pyrid-2-yloxy |
| 178 | Cl | Cl | pyrimidin-2-yloxy |
| 179 | Cl | $CF_3$ | pyrimidin-2-yloxy |
| 180 | $CF_3$ | $CF_3$ | pyrimidin-2-yloxy |
| 181 | $OCF_3$ | $OCF_3$ | 6-chloropyridazin-3-yloxy |

*N-oxide at the 1-position of the piperazine ring.

Compounds of formula I where A is N, forming a piperazine ring; n is 1, forming single bonds from the methyl carbon and its substituents; p, q, and r are 0; m and s are 1; B is a bridging group from the methyl carbon (α) to R; E is $-(CR^{27}R^{28})_x-(CR^{29}R^{30})_y-$, where x is 1, and y is 0; $R^8$ is phenyl substituted with $R^{22}$, $R^{23}$, $R^{24}$, $R^{25}$, and $R^{26}$; and R is phenyl substituted with $R^{17}$, $R^{18}$, $R^{19}$, $R^{20}$, and $R^{21}$; where $R^1$, $R^2$, $R^3$, $R^5$, $R^6$, $R^{21}$, $R^{22}$, $R^{23}$, $R^{25}$, $R^{26}$, $R^{27}$ and $R^{28}$ are hydrogen:

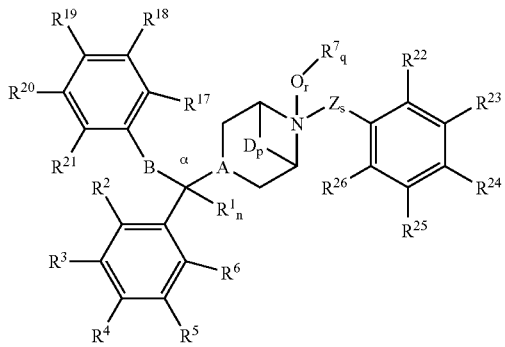

I

| Cmpd. No. | B | $R^4$ | $R^{17}/R^{18}$ | $R^{19}/R^{20}$ | $R^{24}$ |
|---|---|---|---|---|---|
| 182 | $CH_2$ | Cl | H/H | Cl/H | pyrid-2-yl |
| 183 | $OCH_2$ | $CF_3$ | H/H | $CF_3$/H | $CO_2C_2H_5$ |
| 184 | $CH_2O$ | Cl | H/H | Cl/H | $OC_3H_7$ |

TABLE 1-continued

Insecticidal N-substituted-4-(substituted arylmethyl)piperidines and Piperazines

| | | | | | |
|---|---|---|---|---|---|
| 185 | $CH_2O$ | $CF_3$ | H/H | Cl/H | $OC_3H_7$ |
| 186 | $CH_2O$ | $CF_3$ | H/H | $CF_3$/H | $OC_3H_7$ |
| 187 | $CH_2O$ | $OCF_3$ | H/H | $CF_3$/H | $OC_3H_7$ |
| 188 | $CH_2O$ | $CF_3$ | H/H | $CF_3$/H | $CH{=}NOC_2H_5$ |
| 189 | $CH_2O$ | $CF_3$ | H/H | $CF_3$/H | 2-ethyl-2H-tetrazol-5-yl |
| 190 | $CH_2O$ | Cl | H/H | $CF_3$/H | pyrid-2-yloxy |
| 191 | $CH_2OC({=}O)NR^{15}$* | $CF_3$ | H/H | Cl/H | pyrid-2-yloxy |
| 192 | $CH_2OC({=}O)NR^{15}$ | Cl | H/F | H/F | pyrid-2-yloxy |
| 193 | $CH_2OC({=}O)NR^{15}$ | $CF_3$ | H/F | H/F | pyrid-2-yloxy |

*$R^{15}$ is hydrogen in Cmpds. 191-193.
[1] chloride salt,
[2] trifluoroacetate salt,
[3] succinate salt,
[4] tartarate salt,
[5] bromide salt,
[6] oxalate salt,
[7] chloride salt, monohydrate,
[8] ethanesulfonate salt,
[9] ethyl sulfate salt The following table sets forth physical characterizing data for compounds of formula I of the present invention:

TABLE 2

Physical Characteristics

| Cmpd No. | Emperical Formula | Physical State/Melting Point (° C.) |
|---|---|---|
| 1 | $C_{12}H_{15}NO{\cdot}HCl$ | — |
| 2 | $C_{12}H_{14}ClNO{\cdot}HCl$ | Solid, 238-239 |
| 3 | $C_{13}H_{14}F_3NO$ | Solid, 69-74 |
| 4 | $C_{13}H_{16}NO_2{\cdot}HCl$ | Solid, 260-264 |
| 5 | $C_{23}H_{14}F_3NO_2$ | Solid, 86-89 |
| 6 | $C_{13}H_{14}F_3NO_2{\cdot}C_2HF_3O_2$ | Solid, 149-152 |
| 7 | $C_{13}H_{17}NO$ | Liquid |
| 8 | $C_{13}H_{17}NO{\cdot}HCl$ | Solid |
| 9 | $C_{15}H_{18}F_3NO_2$ | Solid, 94.5-97 |
| 10 | $C_{17}H_{22}F_3NO_2$ | Solid, 89-90 |
| 11 | $C_{17}H_{20}F_3NO_2$ | Oil |
| 12 | $C_{20}H_{26}F_3NO_2$ | Solid, 44-45 |
| 13 | $C_{17}H_{22}F_3NO_3$ | Oil |
| 14 | $C_{17}H_{16}FN_3O_3$ | Solid, 137-190 |
| 15 | $C_{24}H_{26}F_3NO_3$ | Gummy Solid |
| 16 | $C_{23}H_{24}FN_3O_2$ | — |
| 17 | $C_{22}H_{20}F_3NO_2S$ | Solid, 129-132 |
| 18 | $C_{23}H_{24}FN_3O_2$ | Solid, 150-152 |
| 19 | $C_{22}H_{21}FN_3O_3{\cdot}C_4H_7O_4$ | Solid, 183-186 |
| 20 | $C_{22}H_{21}FN_3O_3{\cdot}C_4H_7O_6$ | Solid, 183-186 |
| 21 | $C_{19}H_{21}NO$ | Solid, 94-95 |
| 22 | $C_{19}H_{20}FNO$ | Solid |
| 23 | $C_{19}H_{20}FNO$ | Solid, 123-124 |
| 24 | $C_{19}H_{20}FNO$ | Solid, 110-112 |
| 25 | $C_{20}H_{20}F_3NO_2$ | Solid, 34-35 |
| 26 | $C_{20}H_{19}BrF_3NO_2$ | Solid, 86-87 |
| 27 | $C_{20}H_{19}F_4NO_2$ | Solid, 54-56 |
| 28 | $C_{19}H_{19}F_2NO$ | Solid, 106-108 |
| 29 | $C_{21}H_{19}F_3N_2O$ | Solid, 141-142 |
| 30 | $C_{21}H_{20}F_3NO_2$ | Solid, 73-74 |
| 31 | $C_{21}H_{22}F_3NO_3$ | Oil |
| 32 | $C_{21}H_{22}F_3NO_3$ | Liquid |
| 33 | $C_{22}H_{27}NO_3$ | Solid, 107-109 |
| 34 | $C_{20}H_{23}NO_2$ | Solid, 65-67 |
| 35 | $C_{21}H_{22}F_3NO_3$ | Solid, 84-85 |
| 36 | $C_{21}H_{22}F_3NO_3{\cdot}HCl$ | Solid, 209-210.5 |
| 37 | $C_{21}H_{22}F_3NO_2S$ | Solid, 79-81 |
| 38 | $C_{22}H_{27}NO_2$ | Powder, 97-98 |
| 39 | $C_{24}H_{31}NO_2$ | Oil |
| 40 | $C_{23}H_{26}F_3NO_2$ | Crystals, 87-89 |
| 41 | $C_{23}H_{26}F_3NO_2{\cdot}HCl$ | Solid, 195-197 |
| 42 | $C_{25}H_{26}F_7NO_2$ | Liquid |
| 43 | $C_{23}H_{26}F_3NO_3$ | Oil |
| 44 | $C_{23}H_{29}F_3NO_2S$ | Foam |
| 45 | $C_{24}H_{28}F_3NO_3S$ | Liquid |
| 46 | $C_{24}H_{25}F_6NO_2$ | Oil |
| 47 | $C_{23}H_{26}F_3NO_3$ | Solid, 78-80 |
| 48 | $C_{24}H_{28}F_3NO_3$ | Solid, 64-66 |
| 49 | $C_{25}H_{30}F_3NO_3$ | Solid, 42-43 |
| 50 | $C_{22}H_{24}F_3NO_4$ | Solid, 38-39 |
| 51 | $C_{25}H_{28}F_3NO_3$ | Solid, 46-48 |
| 52 | $C_{23}H_{23}ClF_3NO_3$ | Oil |
| 53 | $C_{22}H_{24}ClNO_2$ | Solid, 72.5-75.5 |
| 54 | $C_{23}H_{23}ClF_3NO_3$ | Solid, 51-52 |
| 55 | $C_{25}H_{28}F_3NO_3$ | Solid, 76-78 |
| 56 | $C_{21}H_{20}F_3NO_3$ | Solid, 121-123 |
| 57 | $C_{24}H_{26}F_3NO_4$ | Solid, 70-71 |
| 58 | $C_{23}H_{26}F_3NO_4S$ | Solid, 108-109.5 |
| 59 | $C_{22}H_{23}F_3N_2O_4$ | Solid, 135-136 |
| 60 | $C_{23}H_{25}F_3N_2O_3$ | Oil |
| 61 | $C_{27}H_{25}F_4NO_3$ | Solid, 110-111 |
| 62 | $C_{25}H_{23}F_3N_2O_2$ | Solid, 115-120 |
| 63 | $C_{25}H_{23}F_3N_2O_3$ | Solid, 89-91 |
| 64 | $C_{25}H_{22}ClF_3N_2O_2$ | Solid |
| 65 | $C_{21}H_{22}ClN_5O$ | Solid, 148-150 |
| 66 | $C_{22}H_{22}F_3N_5O$ | Solid, 172-175 |
| 67 | $C_{22}H_{22}F_3N_5O_2$ | Solid, 151-152 |
| 68 | $C_{22}H_{25}N_5O$ | Oil |
| 69 | $C_{21}H_{24}ClN_5O$ | Oil |
| 70 | $C_{22}H_{24}FN_5O$ | Oil |
| 71 | $C_{23}H_{24}F_3N_5O$ | Solid, 120-123 |
| 72 | $C_{23}H_{24}F_3N_5O_2$ | Solid, 120-121 |
| 73 | $C_{23}H_{23}F_4N_5O_2$ | Solid, 105-109 |
| 74 | $C_{28}H_{28}F_3NO_4$ | Gummy solid, 52-55 |
| 75 | $C_{22}H_{21}F_6NO_3$ | Oil |
| 76 | $C_{31}H_{30}ClNO_3$ | Solid, 112-115 |
| 77 | $C_{23}H_{26}F_3NO_3$ | Solid, 167-169 |
| 78 | $C_{23}H_{24}F_3N_5O_2$ | Solid foam, 75-78 |
| 90 | $C_{26}H_{30}F_3N_7O$ | Syrup |
| 91 | $C_{25}H_{30}F_3N_7$ | Solid |
| 92 | $C_{28}H_{29}F_3N_8O$ | Solid, 140-141 |
| 93 | $C_{16}H_{15}ClFN_3S$ | Glassy solid |
| 94 | $C_{30}H_{29}ClF_3N_5O$ | Solid, 125 |
| 95 | $C_{27}H_{31}F_6N_3O_2$ | Solid, 79-83 |
| 96 | $C_{28}H_{27}F_6N_3O_3$ | Syrup |
| 97 | $C_{30}H_{31}F_6N_3O_3$ | Syrup |
| 98 | $C_{30}H_{31}F_6N_3O_3$ | Syrup |
| 99 | $C_{31}H_{33}F_6N_3O_3$ | Syrup |

TABLE 2-continued

Physical Characteristics

| Cmpd No. | Emperical Formula | Physical State/ Melting Point (° C.) |
|---|---|---|
| 100 | $C_{31}H_{31}F_6N_3O_4$ | Syrup |
| 101 | $C_{32}H_{27}ClF_6N_4O_2$ | Syrup |
| 102 | $C_{29}H_{30}F_3N_7O$ | Solid foam, 60-64 |
| 103 | $C_{29}H_{29}ClF_3N_7$ | Oil |
| 104 | $C_{29}H_{29}ClF_3N_7O$ | Oil |
| 105 | $C_{29}H_{29}ClF_3N_7O$ | Oil |
| 106 | $C_{29}H_{29}ClF_3N_7$ | Solid foam, 61-66 |
| 107 | $C_{29}H_{29}BrF_3N_7$ | Solid foam, 74-78 |
| 108 | $C_{29}H_{29}F_4N_7$ | Solid foam, 62-66 |
| 109 | $C_{29}H_{29}F_3IN_7O$ | Solid foam, 88-92 |
| 110 | $C_{29}H_{28}Cl_2F_3N_7O$ | Oil |
| 111 | $C_{29}H_{28}Cl_2F_3N_7O$ | Oil |
| 112 | $C_{29}H_{28}Cl_2F_3N_7O$ | Oil |
| 113 | $C_{30}H_{32}F_3N_7O$ | Solid foam, 80-84 |
| 114 | $C_{32}H_{36}F_3N_7O$ | Solid foam, 62-66 |
| 115 | $C_{33}H_{38}F_3N_7$ | Solid foam, 78-82 |
| 116 | $C_{30}H_{32}F_3N_7O_2$ | Solid foam, 61-65 |
| 117 | $C_{29}H_{27}F_6N_7$ | Foam |
| 118 | $C_{30}H_{29}F_6N_7$ | Solid foam, 70-73 |
| 119 | $C_{30}H_{29}F_6N_7O$ | Solid foam, 62-66 |
| 120 | $C_{30}H_{29}F_6N_7O$ | Syrup |
| 121 | $C_{30}H_{29}F_6N_7O$ | Solid foam, 63-67 |
| 122 | $C_{30}H_{29}F_6N_7O$ | Syrup |
| 123 | $C_{29}H_{27}F_6N_7O_2$ | Semi-solid, 65-70 |
| 124 | $C_{30}H_{29}F_6N_7O_2$ | Solid foam, 59-61 |
| 125 | $C_{29}H_{31}F_3N_8O_3S$ | Solid foam, 95-98 |
| 126 | $C_{29}H_{29}F_3N_8O_3$ | Semi-solid |
| 127 | $C_{31}H_{31}F_6N_7O$ | Syrup |
| 128 | $C_{31}H_{31}F_6N_7O_2$ | Syrup |
| 129 | $C_{30}H_{29}F_6N_7O_3S$ | Solid, 65-68 |
| 130 | $C_{30}H_{29}F_6N_7O_4S$ | Solid, 55-60 |
| 131 | $C_{32}H_{28}ClF_3N_4O_3$ | Oil |
| 132 | $C_{33}H_{28}F_6N_4O_3$ | Solid, 67-74 |
| 133 | $C_{33}H_{28}F_6N_4O_4$ | — |
| 134 | $C_{41}H_{31}F_9N_4O_4$ | Solid |
| 135 | $C_{29}H_{28}F_3N_7O_2$ | Solid foam, 65-70 |
| 136 | $C_{29}H_{27}ClF_3N_7O_2$ | Solid foam, 69-71 |
| 137 | $C_{29}H_{27}ClF_3N_7O_2$ | Solid foam, 62-65 |
| 138 | $C_{28}H_{27}Cl_2N_7O$ | Solid, 143-145 |
| 139 | $C_{29}H_{27}ClF_3N_7O_2$ | Solid foam, 70-74 |
| 140 | $C_{29}H_{27}BrF_3N_7O_2$ | Solid foam, 62-66 |
| 141 | $C_{29}H_{27}F_4N_7O_2$ | Semi-solid |
| 142 | $C_{29}H_{27}F_4N_7O_2$ | Solid foam, 55-58 |
| 143 | $C_{29}H_{27}F_4N_7O_2$ | Solid foam, 68-71 |
| 144 | $C_{29}H_{27}F_3IN_7O_2$ | Solid foam, 88-90 |
| 145 | $C_{30}H_{30}F_3N_7O_2$ | Semi-solid |
| 146 | $C_{30}H_{30}F_3N_7O_3$ | Solid foam, 58-61 |
| 147 | $C_{31}H_{29}F_6N_7O_2$ | Solid, 105-110 |
| 148 | $C_{30}H_{27}F_6N_7O_3$ | Solid foam, 114-120 |
| 149 | $C_{31}H_{29}F_6N_7O_3$ | Syrup |
| 150 | $C_{29}H_{27}F_3N_8O_4$ | Solid foam, 84-87 |
| 151 | $C_{31}H_{29}F_6N_7O_3$ | Solid, 131-134 |
| 152 | $C_{32}H_{31}F_6N_7O_3$ | Solid, 127-130 |
| 153 | $C_{32}H_{33}ClF_3N_7O$ | Solid |
| 154 | $C_{33}H_{33}F_6N_7O$ | Solid, 152-155 |
| 155 | $C_{36}H_{32}F_3N_7O_3$ | — |
| 156 | $C_{36}H_{30}Cl_2F_3N_7O_3$ | Solid foam, 87-92 |
| 157 | $C_{36}H_{30}Cl_2F_3N_7O_3$ | Solid foam, 100-103 |
| 158 | $C_{36}H_{30}Cl_2F_3N_7O_3$ | Solid foam, 110-114 |
| 159 | $C_{36}H_{30}Br_2F_3N_7O_3$ | Solid foam, 109-112 |
| 160 | $C_{36}H_{30}Cl_2F_5N_7O_3$ | Solid foam, 95-100 |
| 161 | $C_{38}H_{36}F_3N_7O_3$ | Solid foam, 101-104 |
| 162 | $C_{38}H_{36}F_3N_7O_5$ | Solid foam, 101-104 |
| 163 | $C_{36}H_{30}F_3N_9O_7$ | Solid foam, 123-128 |
| 164 | $C_{31}H_{30}F_6N_8O_2$ | Solid, 124-128 |
| 165 | $C_{31}H_{30}F_6N_8O_3$ | Solid foam, 65-68 |
| 166 | $C_{31}H_{30}F_6N_8OS$ | Solid, 144-148 |
| 167 | $C_{28}H_{26}Cl_2N_4O$ | Oil |
| 168 | $C_{29}H_{26}ClF_3N_4O$ | Solid |
| 169 | $C_{30}H_{26}F_6N_4O$ | Oil |
| 170 | $C_{30}H_{25}ClF_6N_4O_3$ | Solid, 60-70 |
| 171 | $C_{27}H_{26}F_6N_2O_5$ | Solid, 157-159 |
| 172 | $C_{32}H_{27}F_7N_2O_4$ | Solid, 84-90 |
| 173 | $C_{29}H_{31}ClF_3N_3O_3$ | Solid |
| 174 | $C_{30}H_{31}F_6N_3O_3$ | Solid, 158-160 |
| 175 | $C_{29}H_{28}F_6N_6O$ | Solid, 134-144 |
| 176 | $C_{30}H_{27}ClF_3N_3O_2$ | Solid |
| 177 | $C_{31}H_{27}F_6N_3O_2$ | Oil |
| 178 | $C_{28}H_{26}Cl_2N_4O_2$ | Semi-oil |
| 179 | $C_{29}H_{26}ClF_3N_4O_2$ | Solid |
| 180 | $C_{30}H_{26}F_6N_4O_2$ | Solid |
| 181 | $C_{30}H_{25}ClF_6N_4O_4$ | Solid, 106-118 |
| 190 | $C_{31}H_{29}ClF_3N_3O_2$ | Oil |
| 191 | $C_{32}H_{30}ClF_3N_4O_3$ | Semi-solid |
| 192 | $C_{31}H_{29}ClF_2N_4O_3$ | Oil |
| 193 | $C_{32}H_{29}F_5N_4O_3$ | Semi-solid |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm dia.× 17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvea, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

As set forth in the foregoing Table 3, most of the compounds therein provided 100% mortality and 100% growth inhibition of tobacco budworm.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all

TABLE 3

Insecticidal Activity of Test Compounds Applied to the Surface of the Diet of Tobacco Budworm

| | \multicolumn{10}{c|}{Cmpd. No} |
|---|---|---|---|---|---|---|---|---|---|---|
| | 3 | 27 | 42 | 43 | 47 | 54 | 57 | 60 | 62 | 67 |
| Percent Mortality | 100 | 0 | 100 | 100 | 0 | 100 | 100 | 0 | 100 | 100 |
| Percent Growth Inhibition | 100 | 97 | 100 | 100 | 100 | 100 | 95 | 58 | 95 | 95 |

| | Cmpd. No | | | | | | | | | |
|---|---|---|---|---|---|---|---|---|---|---|
| | 69 | 72 | 77 | 91 | 92 | 94 | 96 | 97 | 98 | 99 |
| Percent Mortality | 0 | 100 | 100 | 0 | 0 | 100 | 100 | 100 | 100 | 100 |
| Percent Growth Inhibition | 99 | 95 | 100 | 79 | 45 | 100 | 96 | 100 | 96 | 96 |

| | Cmpd. No | | | | | | | | | |
|---|---|---|---|---|---|---|---|---|---|---|
| | 100 | 101 | 102 | 103 | 105 | 106 | 107 | 108 | 109 | 111 |
| Percent Mortality | 100 | 100 | 100 | 0 | 100 | 100 | 100 | 100 | 100 | 100 |
| Percent Growth Inhibition | 100 | 100 | 100 | 20 | 100 | 95 | 95 | 94 | 100 | 100 |

| | Cmpd. No | | | | | | | | | |
|---|---|---|---|---|---|---|---|---|---|---|
| | 113 | 114 | 115 | 116 | 117 | 118 | 119 | 120 | 121 | 122 |
| Percent Mortality | 100 | 100 | 17 | 100 | 100 | 100 | 100 | 0 | 100 | 100 |
| Percent Growth Inhibition | 100 | 100 | 39 | 100 | 100 | 96 | 100 | 40 | 100 | 96 |

| | Cmpd. No | | | | | | | | |
|---|---|---|---|---|---|---|---|---|---|
| | 123 | 124 | 125 | 126 | 127 | 128 | 129 | 130 | 131 |
| Percent Mortality | 100 | 100 | 100 | 100 | 100 | 0 | 100 | 100 | 50 |
| Percent Growth Inhibition | 100 | 100 | 100 | 100 | 100 | 96 | 95 | 100 | 100 |

| | Cmpd. No | | | | | | | | |
|---|---|---|---|---|---|---|---|---|---|
| | 132 | 136 | 137 | 138 | 139 | 140 | 142 | 143 | 144 |
| Percent Mortality | 83 | 76 | 100 | 0 | 100 | 100 | 67 | 17 | 100 |
| Percent Growth Inhibition | 100 | 0 | 100 | 14 | 100 | 100 | 100 | 87 | 100 |

| | Cmpd. No | | | | | | | | |
|---|---|---|---|---|---|---|---|---|---|
| | 145 | 146 | 147 | 148 | 149 | 150 | 153 | 156 | 166 |
| Percent Mortality | 100 | 100 | 100 | 100 | 100 | 100 | 100 | 0 | 100 |
| Percent Growth Inhibition | 100 | 100 | 92 | 100 | 96 | 100 | 100 | 28 | 95 |

| | Cmpd. No | | | | | | | | |
|---|---|---|---|---|---|---|---|---|---|
| | 167 | 168 | 169 | 170 | 171 | 172 | 174 | 175 | 176 |
| Percent Mortality | 100 | 100 | 100 | 100 | 0 | 100 | 100 | 100 | 100 |
| Percent Growth Inhibition | 100 | 100 | 100 | 100 | 87 | 100 | 100 | 100 | 100 |

| | Cmpd. No | | | | | | | | |
|---|---|---|---|---|---|---|---|---|---|
| | 177 | 178 | 179 | 180 | 181 | 190 | 191 | 192 | 193 |
| Percent Mortality | 100 | 0 | 100 | 100 | 100 | 100 | 0 | 0 | 0 |
| Percent Growth Inhibition | 100 | 100 | 100 | 100 | 100 | 100 | 54 | 44 | 58 |

These tests were conducted with 0.25 millimoles of candidate insecticide on the surface of the diet

What is claimed is:

1. A compound of the following formula:

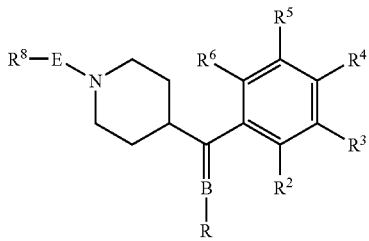

wherein B is NNR$^{15}$C(=O)* or NNR$^{15}$SO$_2$*, where R$^{15}$ is H or alkyl and where the asterisk denotes attachment to R;

R$^2$, R$^3$, R$^4$, R$^5$ and R$^6$ are independently hydrogen, halogen, alkyl, haloalkyl, hydroxyl, alkoxy, haloalkoxy, pentahalothio, alkylthio, cyano, nitro, alkylcarbonyl, alkoxycarbonyl, aryl, or aryloxy, or either of R$^2$ and R$^3$, and R$^3$ and R$^4$ taken together are —OCF$_2$O—, —OCF$_2$CF$_2$—, —CF$_2$CF$_2$O—, or —CH=CHCH=CH—, forming a benzo-fused ring;

R is phenyl substituted with R$^{17}$, R$^{18}$, R$^{19}$, R$^{20}$ and R$^{21}$;

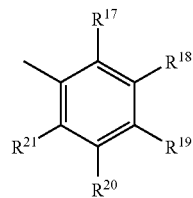

where R$^{17}$, R$^{18}$, R$^{19}$, R$^{20}$ and R$^{21}$ are independently hydrogen, halogen, haloalkyl or haloalkoxy;

E is —C(R$^{27}$)(R$^{28}$), where R$^{27}$ and R$^{28}$ are independently selected from the group consisting of hydrogen, alkyl, and aryl optionally substituted with alkoxy; and R$^8$ is phenyl substituted with R$^{22}$, R$^{23}$, R$^{24}$, R$^{25}$, and R$^{26}$ where R$^{22}$, R$^{23}$, R$^{25}$, and R$^{26}$ are hydrogen

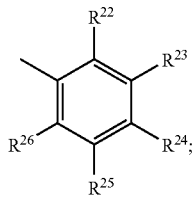

and

R$^{24}$ is selected from the group consisting of hydrogen, halogen, hydroxy, alkoxy, cycloalkylalkoxy, optionally substituted arylalkoxy, cyano, nitro, alkylamino, alkoxycarbonylamino, (alkyl)(alkoxycarbonyl)amino, (heteroaryl)(alkoxycarbonyl)-amino, (heteroaryl)(alkoxycarbonyl)amino, alkoxycarbonyl, optionally substituted aryloxy, optionally substituted 1,2,5-thiadiazolyoxy, optionally substituted 2H-tetrazole, optionally substituted pryidyl, and optionally subsituted pyridyloxy and N-oxides and agriculturally acceptable salts thereof.

2. A compound of claim 1, wherein R$^2$, R$^3$, R$^5$, R$^6$, R$^{17}$, R$^{18}$, R$^{20}$, R$^{21}$, R$^{22}$, R$^{23}$, R$^{25}$ and R$^{26}$ are hydrogen; R$^4$ and R$^{19}$ are difluoromethyl, trifluoromethyl, or trifluoromethoxy, and R$^{24}$ is pyrid-2-yloxy or pyrimidin-2-yloxy.

3. A composition containing an insecticidally effective amount of a compound of claim 1 in admixture with at least one agriculturally acceptable extender or adjuvant.

4. The insecticidal composition of claim 3, further comprising at least one additional insecticide.

5. A composition containing an insecticidally effective amount of a compound of claim 2 in admixture with at least one agriculturally acceptable extender or adjuvant.

6. The insecticidal composition of claim 5, further comprising at least one additional insecticide.

7. A method of controlling tobacco budworm, comprising applying an insecticidally effective amount of a composition of claim 1 to a locus where insects are present or are expected to be present.

8. A method of controlling tobacco budworm, comprising applying an insecticidally effective amount of a composition of claim 2 to a locus where insects are present or are expected to be present.

9. The compound of claim 1, where B is NNR$^{15}$C(=O)*; R$^2$, R$^3$, R$^5$, R$^6$, R$^{27}$ and R$^{28}$ are hydrogen, R$^4$ is —OCF$_3$, and R$^{24}$ is 2-ethyl-2H-tetrazol-5-yl.

* * * * *